(12) United States Patent
Jamieson et al.

(10) Patent No.: US 8,680,021 B2
(45) Date of Patent: *Mar. 25, 2014

(54) ZINC FINGER PROTEINS FOR DNA BINDING AND GENE REGULATION IN PLANTS

(75) Inventors: Andrew Jamieson, San Francisco, CA (US); Guofu Li, Albany, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 695 days.

This patent is subject to a terminal disclaimer.

(21) Appl. No.: 11/511,106

(22) Filed: Aug. 28, 2006

(65) Prior Publication Data

US 2006/0294617 A1    Dec. 28, 2006

Related U.S. Application Data

(63) Continuation of application No. 10/055,713, filed on Jan. 22, 2002, now Pat. No. 7,273,923.

(60) Provisional application No. 60/263,445, filed on Jan. 22, 2001, provisional application No. 60/290,716, filed on May 11, 2001.

(51) Int. Cl.
*C40B 40/06* (2006.01)
(52) U.S. Cl.
USPC ............................................................ 506/26
(58) Field of Classification Search
None
See application file for complete search history.

(56) References Cited

U.S. PATENT DOCUMENTS

| | | | |
|---|---|---|---|
| 4,407,956 A | 10/1983 | Howell |
| 4,536,475 A | 8/1985 | Anderson |
| 4,684,611 A | 8/1987 | Schilperoort et al. |
| 4,945,050 A | 7/1990 | Sanford et al. |
| 4,990,607 A | 2/1991 | Katagiri et al. |
| 5,096,814 A | 3/1992 | Aivasidis et al. |
| 5,096,815 A | 3/1992 | Ladner et al. |
| 5,198,346 A | 3/1993 | Ladner et al. |
| 5,223,409 A | 6/1993 | Ladner et al. |
| 5,243,041 A | 9/1993 | Fernandez-Pol |
| 5,302,519 A | 4/1994 | Blackwood et al. |
| 5,324,638 A | 6/1994 | Tao et al. |
| 5,324,818 A | 6/1994 | Nabel et al. |
| 5,324,819 A | 6/1994 | Oppermann et al. |

(Continued)

FOREIGN PATENT DOCUMENTS

| | | |
|---|---|---|
| EP | 0875567 | 4/1998 |
| GB | 2348424 | 4/2000 |

(Continued)

OTHER PUBLICATIONS

Clemens et al., Journal of Molecular Biology. vol. 244: 23-35; 1994.*

(Continued)

*Primary Examiner* — Christian Boesen
(74) *Attorney, Agent, or Firm* — Pasternak Patent Law; Dahna S. Pasternak

(57) ABSTRACT

Disclosed herein are modified plant zinc finger proteins; compositions comprising modified plant zinc finger proteins and methods of making and using modified plant zinc finger proteins. The modified plant zinc finger proteins, in contrast to naturally-occurring plant zinc finger proteins, have a binding specificity that is determined by tandem arrays of modular zinc finger binding unit.

7 Claims, 3 Drawing Sheets

(56) References Cited

U.S. PATENT DOCUMENTS

| | | | |
|---|---|---|---|
| 5,340,739 | A | 8/1994 | Stevens et al. |
| 5,348,864 | A | 9/1994 | Barbacid et al. |
| 5,350,840 | A | 9/1994 | Call et al. |
| 5,356,802 | A | 10/1994 | Chandrasegaran |
| 5,376,530 | A | 12/1994 | De The et al. |
| 5,403,484 | A | 4/1995 | Ladner et al. |
| 5,436,150 | A | 7/1995 | Chandrasegaran |
| 5,487,994 | A | 1/1996 | Chandrasegaran |
| 5,498,530 | A | 3/1996 | Schatz et al. |
| 5,578,483 | A | 11/1996 | Evans et al. |
| 5,585,245 | A | 12/1996 | Johnsson et al. |
| 5,597,693 | A | 1/1997 | Evans et al. |
| 5,639,592 | A | 6/1997 | Evans et al. |
| 5,674,738 | A | 10/1997 | Abramson et al. |
| 5,702,914 | A | 12/1997 | Evans et al. |
| 5,789,538 | A | 8/1998 | Rebar et al. |
| 5,792,640 | A | 8/1998 | Chandrasegaran |
| 5,792,933 | A | 8/1998 | Ma |
| 5,830,721 | A | 11/1998 | Stemmer et al. |
| 5,866,121 | A | 2/1999 | Coffino et al. |
| 5,869,618 | A | 2/1999 | Lippman et al. |
| 5,871,902 | A | 2/1999 | Weininger et al. |
| 5,871,907 | A | 2/1999 | Winter et al. |
| 5,916,794 | A | 6/1999 | Chandrasegaran |
| 5,939,538 | A | 8/1999 | Leavitt et al. |
| 5,972,615 | A | 10/1999 | An et al. |
| 6,001,885 | A | 12/1999 | Vega et al. |
| 6,007,408 | A | 12/1999 | Sandhu |
| 6,007,988 | A | 12/1999 | Choo et al. |
| 6,013,453 | A | 1/2000 | Choo et al. |
| 6,077,994 | A | 6/2000 | Coupland |
| 6,140,081 | A | 10/2000 | Barbas |
| 6,140,466 | A | 10/2000 | Barbas, III et al. |
| 6,160,091 | A | 12/2000 | Peukert et al. |
| 6,207,446 | B1 | 3/2001 | Szostak et al. |
| 6,242,568 | B1 | 6/2001 | Barbas, III et al. |
| 6,453,242 | B1* | 9/2002 | Eisenberg et al. ............. 702/19 |
| 6,599,692 | B1* | 7/2003 | Case et al. ................ 435/4 |
| 6,706,470 | B2 | 3/2004 | Choo et al. |
| 6,780,590 | B2* | 8/2004 | Case et al. ................ 435/6 |
| 6,824,978 | B1 | 11/2004 | Cox et al. |
| 7,273,923 | B2* | 9/2007 | Jamieson et al. ............. 530/370 |
| 2003/0108880 | A1 | 6/2003 | Rebar et al. |

FOREIGN PATENT DOCUMENTS

| | | |
|---|---|---|
| WO | WO 92/02536 | 2/1992 |
| WO | WO 95/11922 | 5/1995 |
| WO | WO 95/19431 | 7/1995 |
| WO | WO 96/06110 | 2/1996 |
| WO | WO 96/06166 | 2/1996 |
| WO | WO 96/11267 | 4/1996 |
| WO | WO 96/20951 | 7/1996 |
| WO | WO 96/32475 | 10/1996 |
| WO | WO 97/27212 | 7/1997 |
| WO | WO 97/27213 | 7/1997 |
| WO | WO 98/44350 | 10/1998 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 99/07206 | 2/1999 |
| WO | WO 99/16890 | 4/1999 |
| WO | WO 99/36553 | 7/1999 |
| WO | WO 99/40210 | 8/1999 |
| WO | WO 99/41371 | 8/1999 |
| WO | WO 99/42474 | 8/1999 |
| WO | WO 99/45132 | 9/1999 |
| WO | WO 99/47656 | 9/1999 |
| WO | WO 99/48909 | 9/1999 |
| WO | WO 00/23464 | 4/2000 |
| WO | WO 00/27878 | 5/2000 |
| WO | WO 00/41566 | 7/2000 |
| WO | WO 00/42219 | 7/2000 |
| WO | WO 00/47775 | 8/2000 |
| WO | WO 01/83732 | 11/2001 |
| WO | WO 01/83751 | 11/2001 |
| WO | WO 02/066640 A2 | 8/2002 |
| WO | WO 03/016496 A2 | 2/2003 |

OTHER PUBLICATIONS

Abel et al., "Transient Transformation of *Arabidopsis* Leaf Protoplasts: A Versatile Experimental System to Study Gene Expression," Plant Journal, 5: 421-427 (1994).

Agarwal et al., "Stimulation of Transcript Elongation Requires Both the Zinc Finger and RNA Polymerase II Binding Domains of Human TFIIS," Biochemistry 30(31): 7842-7851 (1991).

Antao et al., "A Thermodynamic Study of Unusually Stable RNA and DNA Hairpins," Nucl. Acids. Res. 19(21): 5901-5905 (1991).

Aoyama et al., "A Glucocorticoid-Mediated Transcriptional Induction System in Transgenic Plants," The Plant Journal 11:605-612 (1997).

Barbas, C.F. "Recent Advances in Phage Display," Curr. Opin. Biotech. 4: 526-530 (1993).

Barbas et al., "Assembly of Combinatorial Antibody Libraries on Phage Surfaces: The Gene III Site," PNAS 88: 7978-7982 (1991).

Barbas et al., "Semisynthetic Combinatorial Antibody Libraries: A Chemical Solution to the Diversity Problem," PNAS 89: 4457-4461 (1992).

Beerli et al., "Toward Controlling Gene Expression at Will: Specific Regulation of the ERBB-2/HER-2 Promoter by Using Polydactyl Zinc Finger Proteins Constructed From Modular Building Blocks," PNAS 95: 14628-14633 (1998).

Beerli et al., "Positive and Negative Regulation of Endogenous Genes by Designed Transcription Factors," PNAS 97: 1495-1500 (2000).

Bellefroid et al., "Clustered Organization of Homologous KRAB Zinc-Finger Genes With Enhanced Expressoin in Human T Lymphoid Cells," EMBO J. 12(4): 1363-1374 (1993).

Berg, J.M., "DNA Binding Specificity of Steroid Receptors," Cell 57: 1065-1068 (1989).

Berg, J.M., "SP1 and the Subfamily of Zinc-Finger Proteins With Guanine-Rich Binding Sites," PNAS 89: 11109-11110 (1992).

Berg et al., "The Galvanization of Biology: A Growing Appreciation for the Roles of Zinc," Science 271: 1081-1085 (1996).

Berg, J.M., "Letting Your Fingers Do the Walking," Nature Biotechnology 15: 323 (1997).

Bergqvist et al., "Loss of DNA-Binding and New Transcriptional Trans-Activation Function in Polyomavirus Large T—Antigen With Mutation of Zinc Finger Motif," Nuc. Acid Res. 18(9): 2715-2720 (1990).

Bevan et al., "T-DNA of the *Agrobacterium* $T_1$ and $R_1$ Plasmids," Ann. Rev. Genet. 16: 357-384 (1982).

Bevan et al., "Binary *Agrobacterium* Vectors for Plant Transformation," Nucleic Acid. Res. 12: 8711-8721 (1984).

Bevan et al., "The Structure and Transcription Start Site of a Major Potato Tuber Protein Gene,"Nucleic Acids Res. 14: 4625-4638 (1986).

Bird et al., "Methylation-Induced Repression—Belts, Braces, and Chromatin," Cell 99: 451-454 (1999).

Bitko et al., "Persistent Activation of RELA by Respiratory Syncytial Virus Involves Protein Kinase C, Underphosphorylated IKBB, and Sequestration of Protein Phosphatase 2A by the Viral Phosphoprotein," J. Virol. 72:5610-5618 (1998).

Blackburn, "Engineering and Design: Rational Versus Combinatorial Approaches," Curr. Opin. Struct. Biol. 10:399-400 (2000).

Blaese et al., "Vectors in Cancer Therapy: How Will They Deliver?" Cancer Gene Therapy 2(4): 291-297 (1995).

Bock et al., "Sleneoprotein Synthesis: An Expansion of the Genetic Code," Trends Biochem. Sci. 16:463-467 (1991).

Bonde et al., "Ontogeny of the V-ERBA Oncoprotein From the Thyroid Hormone Receptor: An Alteration in the DNA Binding Domain Plays a Role Crucial for VERBA Function," J. Virology 65(4): 2037-2046 (1991).

(56) References Cited

OTHER PUBLICATIONS

Bray, "Expression of the B-Subunit of B-Conglycinin in Seeds of Transgenic Plants," Planta 172: 364-370 (1987).
Brisson et al., "Expression of a Bacterial Gene in Plants by Using a Viral Vector" Nature 310:511-514 (1984).
Broglie et al., "Light-Regulated Expression of a Pea Ribulose-1,5-Bisphosphate Carboxylase Small Subunit Gene in Transformed Plant Cells," Science 224:838-843 (1984).
Caponigro et al., "Transdomination Genetic Analysis of a Growth Control Pathway," PNAS 95: 7508-7513 (1998).
Celenza et al., "A Yeast Gene That Is Essential for Release From Glucose Repression Encodes a Protein Kinase," Science 233: 1175-1180 (1986).
Cheng et al., "Identification of Potential Target Genes for ADRIP Through Characterization of Essential Nucleotides in UAS1," Mol. Cellular Biol. 14(6): 3842-3852 (1994).
Cheng et al., "A Single Amino Acid Subsitution in Zinc Finger 2 of ADRIP Changes Its Binding Specificity at Two Positions in UAS1," J. Mol. Boil. 251: 1-8 (1995).
Chern et al., "The Regulator of MAT2 (ROM2) Protein Binds to Early Maturation Promoters and Represses PVALF-Activated Transcription," Plant Cell 8: 305-321 (1996).
Cho et al., "Analysis of the C-Terminal Region of *Arabidopsis thalania* Apetala1 as a Transcription Activation Domain," Plant Mol. Biol. 40:419-429 (1999).
Choo et al., "Designing DNA-Binding Proteins on the Surface of Filamentous Phage," Curr. Opin. Biotechnology 6: 431-436 (1995).
Choo et al., "Physicial Basis of Protein-DNA Recognition Code," Curr. Opin. Struct. Biol. 7(1): 117-125 (1997).
Choo et al,. "Advances in Zinc Finger Engineering," Curr. Opin. Struct. Biol. 10:411-416 (2000).
Choo et al., "Promoter-Specific Activiation of Gene Expression Directed by Bacteriophage-Selected Zinc Fingers," J. Mol. Biol. 273: 525-532 (1997).
Choo et al., "In Vivo Repression by a Site-Specific DNA-Binding Protein Deisned Against an Onogenic Sequence," Nature 372: 642-645 (1994).
Choo et al., "All Wrapped Up," Nature Struct. Biol. 5(4): 253-255 (1998).
Choo, Y., "Recognition of DNA Methylation by Zinc Fingers," Nature Struct. Biol. 5(4): 264-265 (1998).
Choo, Y., "End Effects in DNA Recognition by Zinc Finger Arrays," Nuc. Acids. Res. 26(2): 554-557 (1998).
Choo et al., "A Role in DNA-Binding for the Linker Sequences of the First Three Zinc Fingers of TFIIIA" Nuc. Acids Res. 21(15): 3341-3346 (1993).
Choo et al., "Toward a Code for the Interactions of Zinc Fingers With DNA: Selection of Randomized Fingers Displayed on Phage," PNAS 91: 11163-11167 (1994).
Choo et al., "Selection of DNA Binding Sites for Zinc Fingers Using Rationally Randomized DNA Reveals Coded Interactions," PNAS 91: 11168-11172 (1994).
Christensen et al., "Maize Polyubiquitin Genes: Structure, Thermal Perturbation of Expression and Transcript Splicing, and Promoter Activity Following Transfer TP Ptotoplasts by Electroporation," Plant Mol. Biol. 18:675-689 (1992).
Cirillo et al., "Binding of the Winged-Helix Transcription Factor HNF3 to a Linker Histone Site on the Nucleosome," EMBO J. 17: 244-254 (1998).
Clark-Curtiss et al., "Analysis of Recombinant DNA Using *Escherichia coli* Minicells," in Methods in Enzymology 101:347-362 (Wu et al., eds) (1983).
Clarke et al., "Zinc Fingers in Caenorhabditis Elegans: Finding Familiies and Probing Patheways," Science 282: 2018-2022 (1998).
Colley et al., "Conversion of a Golgi Apparatus Sialtransferase to a Secretory Protein by Replacement of the NH2-Terminal Signal Anchor With a Signal Peptide," J. Biol. Chem. 264:17619-17622 (1989).

Collingwood et al., "Nuclear Receptors: Coactivators, Corepressors and Chromatin Remodeling in the Control of Transcription," J. Mol. Endocrinol. 23: 255-275 (1999).
Corbi et al., "Synthesis of a New Zinc Finger Peptide: Comparison of Its "Code" Deduced and "Casting" Derived Binding Sites," FEBS Letters 417: 71-74 (1997).
Cordingley et al., "Steroid-Dependent Interaction of Transcription Factors With the Inducible Promoter of Mouse Mammary Tumor Virus In Vivo," Cell 48: 261-270 (1987).
Crossway et al., "Micromanipulation Techniques in Plant Biotechnology," Biotechniques 4: 320-334 (1986).
Crozatier et al., "Single Amino Acid Exchanges in Separate Domains of the *Drosophila* Serendipity Zinc Finger Protein Cause Embroyonic and Sex Biased Lethality," Genetics 131: 905-916 (1992).
Cruz et al., "Cell-to-Cell and Phloem-Mediated Transport of Potato Virus X. The Role of Virions," Plant Cell 10:495-510 (1998).
Damm et al., "Protein Encoded by V-erbA Functions As a Thyroid-Hormone Receptor Antagonist," Nature 339:593-597 (1989).
Debs et al., "Regulation of Gene Expression In Vivo by Liposome-Mediated Delivery of a Purified Transcription Factor," J. Biological Chemistry 265(18): 10189-10192 (1990).
DesJardins et al., "Repeated CT Elements Bound by Zinc Finger Proteins Control the Absolute and Relative Activities of the Two Principal Human C-MYC Promoters," Mol. Cell. Biol. 13(9): 5710-5724 (1993).
Desjarlais et al., "Redesigning the DNA-Binding Specificity of a Zinc Finger Protein: A Data Base-Guided Approach," Proteins: Structure, Function, and Genetics 12(2): 101-104 (1992).
Desjarlais et al., "Redesigning the DNA-Binding Specificity of a Zinc Finger Protein: A Data Base-Guided Approach," Proteins: Structure, Function, and Genetics 13(3): 272 (1992).
Desjarlais et al., "Toward Rules Relating Zinc Finger Protein Sequences and DNA Binding Site Perferences," PNAS 90: 7345-7349 (1992).
Desjarlais et al., "Use of a Zinc-Finger Consensus Sequence Framework and Specificity Rules to Design Specific DNA Binding, Proteins" PNAS 90: 2256-2260 (1993).
Desjarlais et al., "Length-Encoded Multiplex Binding Site Determination: Application to Zinc Finger Proteins," PNAS 91: 11099-11103 (1994).
D'Halluin et al., "Transgenic Maize Plants by Tissue Electroporation," Plant Cell 4:1495-1505 (1992).
Dibello et al., "The *Drosophila* Broad-Complex Encodes a Family of Related Proteins Containing Zinc Fingers," Genetics 129: 385-397 (1991).
Donze et al., "Activation of Delta-Globin Gene Expression by Erythroid Krupple-Like Factor: A Potential Approach for Gene Therapy of Sickle Cell Disease," Blood 88: 4051-4057 (1996).
Doyle & Hunt, "Reduced Nuclear Factor Kb (p65) Expression in Rat Primary Sensory Neurons After Peripheral Nerve Injury," Neuroreport 8:2937-2942 (1997).
Dudley et al., "Using RNA Interference to Identify Genes Required for RNA Interference," PNAS USA 99(7):4191-4196 (2002).
Duering, K., "Synthesis and Self-Assembly of a Functional Monoclonal Antibody in Transgenic *Nicotiana tabacum*," Plant Molecular Biology 15: 281-294 (1990).
Elrod-Erickson et al., "ZIF268 Protein-DNA Complex Refined At 1.6: A Model System for Understanding Zinc Finger-DNA Interactions," Structure 4(10): 1171-1180 (1996).
Elrod-Erickson et al., "High-Resolution Structures of Variant ZIF268-DNA Complexes: Implications for Understanding Zinc Finger-DNA Recognition," Structure 6(4): 451-464 (1998).
Englbrecht, et al. "Conservation, Diversification and Expansion of C2H2 Zinc Finger Proteins in the *Arabidopis thaliana* Genome," BioMed Genomics 5:39 (2004).
Evans, "The v-erbA Oncogene Is a Thyroid Hormone Receptor Antagonist," Int. J. Cancer Suppl. 4: 26-28 (1989).
Fairall et al., "The Crystal Structure of a Two Zinc-Finger Peptide Reveals an Extension to the Rules for Zinc-Finger/ DNA Recognition," Nature 366: 483-487 (1993).
Fields et al., "A Novel Genetic System to Detect Protein-Protein Interactions," Nature 340:245-246 (1989).

(56) References Cited

OTHER PUBLICATIONS

Frankel et al., "Fingering Too Many Proteins," Cell 53: 675 (1988).
Friesen et al., "Phage Display of RNA Binding Zinc Fingers From Transcription Factor IIIA," J. Biological Chem. 272(17): 10994-10997 (1997).
Friesen et al., "Specific RNA Binding Proteins Constructed From Zinc Fingers," Nature Structural Biology 5(7): 543-546 (1998).
Fromm et al., "Expression of Genes Transferred Into Monocot and Dicot Plant Cells by Electroporation," Proc. Nat. Acad. Sci. USA 82:5824-5828 (1985).
Ghosh, "A Relational Database of Teranscription Factors," Nucleic Acids Res. 18: 1749-1756 (1990).
Gillemans et al., "Altered DNA Binding Specificity Mutants of EKLF and SPI Show That EKLF Is an Activator of the B-Globin Locus Control Region In Vivo," Genes and Development 12: 2863-2873 (1998).
Goff et al., "Transactivation of Anthocyanin Bisynthetic Genes Following Transfer of B Regulatory Genes Into Maize Tissues," EMBO J. 9:2517-2522 (1990).
Goff et al., "Identification of Functional Domains in the Maize Transcriptional Activator C1: Comparison of Wild-Type and Dominant Inhibitor Proteins," Genes Dev. 5:298-309 (1991).
Gogos et al., "Recognition of Diverse Sequences by Class 1 Zinc Fingers: Asymmetries and Indirect Effects on Specificty in the Interaction Between CF2II and A+T-Rich Sequence Elements," PNAS 93(5): 2159-2164 (1996).
Gong et al., "A Constitutively Expressed Myc-Like Gene Involved in Anthocyanin Biosynthesis From Perilla Frutescens: Molecular Characterization, Heterologous Expression Plants and Transactivation in Yeast Cells," Plant Mol. Biol. 41:33-44 (1999).
Gordon-Kamm et al., "Transformation of Maize Cells and Regeneration of Fertile Transgenic Plants," Plant Cell 2: 603-618 (1990).
Gossen et al.., "Tight Control of Gene Expression in Mammalian Cells by Tetracycline-Responsive Promoters,"PNAS 89:5547-5551 (1992).
Greisman et al., "A General Strategy for Selecting High-Affinity Zinc Finger Proteins for Diverse DNA Target Sites," Science 275: 657-661 (1997).
Grierson and Corey, Plant Molecular Biology, 2d Ed., Blackie, London, Ch. 7-9 (1988).
Gurley et al., "Upstream Sequences Required for Efficient Expression of a Soybean Heat Shock Gene," Molecular and Cellular Biology 6:559-565 (1986).
Hagmann et al., "The VP16 Paradox: Herpes Simplex Virus VP16 Contains a Long-Range Activation Domain But Within the Natural Multiprotein Complex Activates Only From Promoter-Proximal Positions," J. Virol. 71: 5952-5962 (1997).
Hall et al., "Functional Interaction Between the Two Zinc Finger Domains of the V-ERBA Oncoprotein," Cell Growth & Differentiation 3: 207-216 (1992).
Hamilton et al., "High Affinity Binding Sites for the Wilms' Tumor Suppressor Protein WTI," Nuc. Acids. Res. 23(2): 277-284 (1995).
Hamilton et al., "Comparison of the DNA Binding Characteristics of the Related Zinc Finger Proteins WT1 and EGRI" Biochemistry 37: 2051-2058 (1998).
Hanas et al., "Internal Deletion Mutants of *Xenopus* Transcription Factor IIIA," Nuc. Acids. Res. 17(23): 9861-9870 (1989).
Hayes et al., "Locations of Contacts Between Individual Zinc Fingers *Xenopus laevis* Transcription Factor IIIA and the Internal Control Region of a 5S RNA Gene," Biochemistry 31: 11600-11605 (1992).
Hein M B et al., "Evaluation of Immunoglobulins From Plant Cells," Biotechnology Progress 7: 455-461 (1991).
Heinzel et al., "A Complex Containing N-CoR, Msin3 and Histone Deacetyiase Medates Transcriptional Repression," Nature 387: 43-48 (1997).
Hendrich et al., "Genomic Structure and Chromosomal Mapping of the Murine and Human Mdb1, Mdb2, Mdb3, and Mdb4 Genes," Mamm Genome 10:906-912 for description of MBD proteins (1999).

Hemalsteen et al., "An Agrobacterium-Transformed Cell Culture From the Monocot Asparagus Officinalis," EMBO J 3:3039-3041 (1984).
Hiatt A et al., "Monoclonal Antibody Engineering in Plants," FEBS Letters 307:71-75 (1992).
Hinchee et al., "Production of Transgenic Soybean Plants Using Agrobacterium-mediated DNA Transfer," Biotechnology 6:915-921 (1988).
Hirst et al., "Discrimination of DNA Response Elements for Thyroid Hormone and Estrogen Is Dependent on Dimerization of Receptor DNA Binding Domains," PNAS 89: 5527-5531 (1992).
Hobo et al., "A BZIP Factor, TRAB1, Interacts With VPI and Mediates Abscisic Acid-Induced Transcription," Proc. Natl. Acad. Sci. USA 96:15,348-15,353 (1999).
Hoffman et al., "Structures of DNA-Binding Mutant Zinc Finger Domains: Implications for DNA Binding," Protein Science 2: 951-965 (1993).
Horsch et al., "A Simple and General Method for Transferring Genes to Plants," Science 227:1229-1231 (1985).
Iida et al. "A Zinc Finger Protein RHL41 Mediated the Light Acclimatization Response in *Arabidopsis*," Plant J. 24(2):191-203 (2000).
Imhof et al., "Transcriptional Regulation of the AP-2ALPHA Promoter by BTEB-1 and AP-2REP, a Novel WT-1/EGR-Related Zinc Finger Repressor," Molecular and Cellular Biology 19(1): 194-204 (1999).
Ishiwatari et al., "Rice Phloem Thioredoxin h Has the Capacity to Mediate Its Own Cell-to-Cell Transport Through Plasmodesmata," Planta 205:12-22 (1998).
Isalan et al., "Synergy Between Adjacent Zinc Fingers in Sequence-Specific DNA Recognition," PNAS 94(11): 5617-5621 (1997).
Isalan et al., "Comprehensive DNA Recognition Through Concerted Interactions From Adjacent Zinc Fingers," Biochemistry 37: 12026-12033 (1998).
Jacobs, G. H., "Determination of the Base Recognition Positions of Zinc Fingers From Sequence Analysis," EMBO J. 11(12): 4507-4517 (1992).
Jamieson et al., "A Zinc Finger Directory for High-Affinity DNA Recognition," PNAS 93: 12834-12839 (1996).
Jamieson et al., "In Vitro Selection of Zinc Fingers With Altered DNA-Binding Specificity" Biochemistry 33: 5689-5695 (1994).
Jefferson, "Asaying Chimeric Genes in Plants: The Gus Gene Fusion System," Plant Molec Biol. Rep 5:387-405), (1987).
Jiang et al., "A Novel Family of CYS-CYS, HIS-CYS Zinc Finger Transcription Factors Expressed in Developing Nervous System and Pituitary Gland," J. Biol. Chem. 271:10723-10730 (1996).
Jones et al., "Replacing the Complementarity-Determining Regions in a Human Antibody With Those From Mouse," Nature 321: 522-525 (1986).
Joung et al., "A Bacterial Two-Hybrid Selection System for Studying Protein-DNA and Protein-Protein Interactions," Proc. Natl. Acad. Sci. USA 97:7382-7387 (2000).
Julian et al., "Replacement of HIS23 by CYS in a Zinc Finger of HIV-1NCP7 Led to a Change in 1H NMR-Derived 3D Structure and to a Loss of Biological Activity," FEBS Letters 331(1,2): 43-48 (1993).
Kaeppler et al., "Silicon Carbide Fiber-Mediated DNA Delivery Into Plant Cells," Plant Cell Reporter 9:415-418 (1990).
Kamiuchi et al., "New Multi Zinc Finger Protein: Biosynthetic Design and Characteristics of DNA Recognition," Nucleic Acids Symposium Series 37: 153-154 (1997).
Kang et al., "Zinc Finger Proteins As Designer Transcription Factors," J. Biol. Chem. 275(12): 8742-8748 (2000).
Kasten et al. "The Plastome-Encoded ZFPA Gene of a Moss Contains Procaryotic as Well as Eukaryotic Promoter Consensus Sequences and Its RNA Abundance Is Modulated by Cyokinin," Curr. Genet. 22:327-333 (1992).
Kay et al., "Duplication of CaMV 35S Promoter Sequences Creates a Strong Enhancer for Plant Genes," Science 236:1299 (1987).
Kim et al., "Serine at Position 2 in the DNA Recognition Helix of a CYS2-HIS2 Zinc Finger Peptide Is Not, in General, Responsible for Base Recognition," J. Mol. Biol. 252: 1-5 (1995).

(56) References Cited

OTHER PUBLICATIONS

Kim et al., "A 2.2 A° Resolution Crystal Structure of a Designed Zinc Finger Protein Bound to DNA," Nat. Struct. Biol. 3(11): 940-945 (1996).
Kim et al., "Design of TATA Box-Binding Protein/Zinc Finger Fusions for Targeted Regulation of Gene Expression," PNAS 94: 3616-3620 (1997).
Kim et al., "Hybrid Restriction Enzymes: Zinc Finger Fusions FOK 1 Cleavage Domain," PNAS 93: 1156-1160 (1996).
Kim et al., "Transcriptional Repression by Zinc Finger Peptides. Exploring the Potential for Application in Gene Therapy" J. Biol. Chem. 272: 29795-29800 (1997).
Kim et al., "Getting a Handhold on DNA: Design of Poly-Zinc Finger Proteins With Femtomolar Dissociation Constants," PNAS 95: 2812-2817 (1998).
Kinzler et al., "The GLI Gene Is a Member of the Kruppel Family of Zinc Finger Proteins," Nature 332: 371-374 (1988).
Klein et al., "Transfer of Foreign Genes Into Intact Maize Cells With High-Velocity Microprojectiles," Proc. Nat. Acad. Sci. USA 85:4305-4309 (1983).
Klug et al. "Zinc Fingers," FASEB 9:597-604 (1995).
Klug, A. "Gene Regulatory Proteins and Their Interaction With DNA," Ann. NY Acad. Sci. 758: 143-160 (1995).
Klug, "Zinc Finger Peptides for the Regulation of Gene Expression," J. Mol. Biol. 293: 215-218 (1999).
Knoepfler et al., "SIN Meets NURD and Other Tails of Repression," Cell 99: 447-450 (1999).
Kothekar, "Computer Simulation of Zinc Finger MOTIFs From Cellular Nucleic Acid Binding Proteins and Their Interaction With Consensus DNA Sequences," FEBS Letters 274(1,2): 217-222 (1990).
Kriwacki et al., "Sequence-Specific Recognition of DNA by Zinc Finger Peptides Derived From the Transcription Factor SP-1," PNAS 89: 9759-9763 (1992).
Kudla et al., "The Regulatory Gene Area Mediating Nitrogen Metabolite R in Aspergillus Nidulans Mutations Affecting Specificity of Gene Activation Alter a Loop Residue of Putative Zinc Finger," EMBO J. 9(5): 1355-1364 (1990).
Laird-Offringa et al., "RNA-Binding Proteins Tamed," Nat. Structural Biol. 5(8): 665-668 (1998).
Lemon et al., "Nuclear Receptor Cofactors As Chromatin Remodelers," Curr. Opin. Genet. Dev. 9:499-504 (1999).
Leo et al., "The SRC Family of Nuclear Receptor Coactivators," Gene 245:1-11 (2000).
Liu et al., "Suppression of Growth and Transformation and Induction of Apoptosis by EGR-1," Cancer Gene Ther. 5:3-28 (1998).
Liu et al., "Design of Polydactyl Zinc-Finger Proteins for Unique Addressing Within Complex Genomes," PNAS 94: 5525-5530 (1997).
Liu et al., "Transcription Factor EGR-1 Suppresses the Growth and Transformation of Human HT-1080 Fibrosarcoma Cells by Induction of Transforming Growth Factor Beta 1," PNAS 93(21): 11831-11836 (1996).
Liu et al, "Regulation of an Endogeous Locus Using a Panel of Designed Zinc Finger Proteins Targeted to Accessible Chromatin Regions: Activation of Vascular Endothelial Growth Factor A," Journal of Biological Chemistry 276(14): 11323-11334 (2001).
Ma, "Assembly of Monoclonal Antibodies With IgG1 and IgA Heavy Chain Domains in Transgenic Tobacco Plants," J K C et al., Eur J Immunology 24: 131-138 (1994).
Mackay et al. "Zinc Fingers Sticking Together," Trends in Biochem. Sci. 23:1-4 (Jan. 1998).
Malik et al., "Transcriptional Regulation Through Mediator-Like Coactivators in Yeast and Metazoan Cells," Trends Biochem. Sci. 25:277-283 (2000).
Mandel-Gutfreund et al., "Quantitative Parameters for Amino Acid-Base Interaction: Implications for Predication of Protein-DNA Binding Sites," Nuc. Acids Res. 26(10): 2306-2312 (1998).
Manteuffel-Cymborowska, "Nuclear Receptors, Their Coactivators and Modulation of Transcription," Acta Biochim. Pol. 46:77-89 (1999).

Margolin et al., "Kruppel-Associated Boxes Are Potent Transcriptional Repression Domains," PNAS 91: 4509-4513 (1994).
McElroy et al., "Isolation of an Efficient Actin Promoter for Use in Rice Transformation," Plant Cell 2:163-171;(1990).
McKenna et al., "Nuclear Receptor Coactivators: Multiple Enzymes, Multiple Complexex, Multiple Functions," J. Steroid Biochem. Mol. Biol. 69:3-12 (1999).
Medberry et al., "IInstructions to Authors: Plant Molecular Biology Reporter," Plant Cell 4:195-192 (1992).
Meissner et al. "Isolation and Characterisation of a Diverse Family of *Arabidopsis* Two and Three-Fingered C2H2 Zinc Finger Protein Genes and CDNAS," Plant Mol. Biol. 33:615-624 (1997).
Miller et al., "Repetitive Zinc-Binding Domains in the Protein Transcriptionfactor IIIA From *Xenopus oocytes*," EMBO J. 4:1609-1614 (1985).
Mistili & Spector, "Applications of the Green Flourescent Protein in Cell Biology and Biotechnology," Nature Biotechnology 15:961-964 (1997).
Mizushima et al., "PEF-BOS, a Powerful Mammilian Expression Vector," Nuc. Acids. Res. 18(17): 5322 (1990).
Morrison, "Transformation in *Escherichia coli*: Cryogenic Prseservation of Competent Cells," J. Bacteriol. 132: 349-351 (1977).
Mukhopadhyay et al., "The Von Hippel-Lindau Tumor Suppressor Gene Product Interacts With SP1 to Repress Vascular Endothelial Growth Factor Promoter Activity" Mol. Cell. Biol. 17(9): 5629-5639 (1997).
Muller-Rober et al., "One of Two Different ADP-Glucose Pyrophosphorylase Genes From Potato Responds Strongly to Elevated Levels of Sucrose," Mol. Gen. Genet. 224: 136-46 (1990).
Nakagama et al, "Sequence and Structural Requirements for High-Affinity DNA Binding by the WTI Gene Product," Molecular and Cellular Biology 15(3): 1489-1498 (1995).
Nardelli et al., "Zinc Finger-DNA Recognition: Analysis of Base Specificity by Site-Directed Mutagenesis," Nucleic Acids Research 20(16): 4137-4144 (1992).
Nardelli et al., "Base Sequence Discrimination by Zinc-Finger DNA-Binding Domains," Nature 349: 175-178 (1991).
Nasim et al., "Eukaryoyic Selenocysteine Incorporation Follows a Nonprocessive Mechanism That Competes With Translational Termination," J. Biol. Chem. 275:14,846-14,852 (2000).
Neering et al., "Transduction of Primitive Human Hematopoietic Cells With Recombinant Adenovirus Vectors," Blood 88:1147-1155 (1996).
Nekludova et al., "Distinctive DNA Conformation With Enlarged Major Groove Is Found in Zn-Finger-DNA and Other Protein-DNA Complexes," PNAS 91: 6948-6952 (1994).
Ogawa et al., "Rice Gibberellin-Insensitive Gene Homolog, OsGAI, Encodes a Nuclear-Localized Protein Capable of Gene Activation at Transcriptional Level," Gene 245:21-29 (2000).
Okanami et al., Half-1 a bZIP-Type Protein, Interacting With the Wheat Transcription Factor HBP-1A Contains a Novel Transcriptional Activation Domain, Genes Cells 1:87-99 (1996).
Oligino et al., "Drug Inducible Transgene Expression in Brain Using a Herpes Simplex Virus Vector," Gene Ther. 5:491-496 (1998).
Oparka et al., "Gating of Epidermal Plasmodesmata Is Restricted to the Leading Edge of Expanding Infection Sites of Tobacco Mosaic Virus (TMV)," Plant J. 12: 781-789 (1997).
Orkin et al., "Report and Recommendations of the Panel to Assess the NIH Investment in Research on Gene Therapy," (Dec. 7, 1995).
Ow et al., "Transient and Stable Expression of the Firefly Luciferase Gene in Plant Cells and Transgenic Plants," Science 234:856-859 (1986).
Pabo et al., "Systematic Analysis of Possible Hydrogen Bonds Between Amino Acid Side Chains and B-Form DNA," J. Biomolecular Struct. Dynamics 1: 1039-1049 (1983).
Pabo et al., Protein-DNA Recognition, Ann. Rev. Biochem. 53: 293-321 (1984).
Pabo, C.O., "Transcription Factors: Structural Families and Principles of DNA Recognition," Ann. Rev. Biochem. 61: 1053-1095 (1992).

(56) References Cited

OTHER PUBLICATIONS

Pain et al., "The Carbonic Anhydrase II Gene, a Gene Regulated by Thyroid Hormone and Erythropoietin, Is Repressed by v-erbA Oncogene in Erythrocytic Cells," New Biol. 2:284-294 (1990).

Palva et al., "Secretion of Interferon by *Bacillus subtilis*," Gene 22:229-235 (1983).

Paszkowski et al., "Direct Gene Transfer to Plants," EMBO J 3: 2717-2722 (1984).

Pavletich et al., "Crystal Structure of a Five-Finger GLI-DNA Complex: New Perspectives on Zinc Fingers," Science, 261: 1701-1707 (1993).

Pavletich et al., "Zinc Finger-DNA Recognition: Crystal Structure of a ZIF268-DNA Complex at 2.1A," Science 252: 809-817 (1991).

Pedersen et al., "Cloning and Sequence Analysis Reveal Structural Variation Among Related Zein Genes in Maize," Cell 29: 1015-1026 (1982).

Pengue et al., "Repression of Transcriptional Activity at a Distance by the Evolutionarily Conserved KRAB Domain Present in a Subfamily of Zinc Finger Proteins," Nuc. Acids Res. 22(15): 2908-2914 (1994).

Pengue et al., "Transcriptional Silencing of Human Immunodeficiency Virus Type 1 Long Terminal Repeat-Driven Gene Expression by the Kruppel-Associated Box Repressor Domain Targeted to the Transactivating Response Element," J. Virology 69(10): 6577-6580 (1995).

Pengue et al., "Kruppel-Associated Box-Mediated Repression of RNA Polymerase II Promoters Is Influenced by the Arrangement of Basal Promoter Elements," PNAS 93: 1015-1020 (1996).

Pina et al., "Nucleosome Positioning Modulates Accessibility of Regulatory Proteins to the Mouse Mammary Tumor Virus Promoter," Cell 60:719-731 (1990).

Pomerantz et al., "Analysis of Homeodomain Function by Structure-Based Design of a Transcription Factor," PNAS 92: 9752-9756 (1995).

Pomerantz et al., "Structure-Based Design of a Dimeric Zinc Finger Protein," Biochemistry 37(4): 965-970 (1998).

Pomerantz et al., "Structure-Based Design of Transcription Factors," Science 267: 93-96 (1995).

Potrykus et al., "Molecular and General Genetics of a Hybrid Foreign Gene Introduced Into Tobacco by Direct Gene Transfer," Molec. Gen. Genet. 199:169-177 (1985).

Qian et al., "Two-Dimensional NMR Studies of the Zinc Finger MOTIF: Solution Structures and Dynamics of Mutant ZFY Domains Containing Aromatic Substitutions in the Hydrophobic Core," Biochemistry 31: 7463-7476 (1992).

Quigley et al., "Complete Androgen Insensitivity Due to Deletion of Exon C of the Androgen Receptor Gene Highlights the Functional Importance of the Second Zinc Finger of the Androgen Receptor In Vivo," Molecular Endocrinology 6(7): 1103-1112 (1992).

Rauscher et al., "Binding of the Wilms' Fumor Locus Zinc Finger Protein to the EGR-I Consensus Sequence," Science 250: 1259-1262 (1990).

Ray et al., "Repressor to Activator Switch by Mutations in the First Zn Finger of the Glucocorticoid Receptor: Is Direct DNA Binding Necessary?" PNAS 88: 7086-7090 (1991).

Rebar et al., "Phage Display Methods for Selecting Zinc Finger Proteins With Novel DNA-Binding Specificities," Methods in Enzymology 267: 129-149 (1996).

Rebar et al, "Zinc Finger Phage: Affinity Selection of Fingers With New DNA-Binding Specifies," Science 263: 671-673 (1994).

Reith et al, "Cloning of the Major Histocompatibility Complex Class II Promoter Binding Protein Affected in a Hereditary Defect in Class II Gene Regulation," PNAS 86: 4200-4204 (1989).

Rendahl et al., "Regulation of Gene Expression In Vivo Following Transduction by Two Separate RAAV Vectors," Nat. Biotechnol. 16:757-761 (1998).

Rhodes et al., "Zinc Fingers: They Play a Key Part in Regulating the Activity of Genes in Many Species, From Yeast to Humans. Fewer Than 10 Years Ago No One Knew They Existed." Scientific American 268:L 56-65 (1993).

Rice et al., "Inhibitors of HIV Nucleocapsid Protein Zinc Fingers As Candidates for the Treatment of AIDS," Science 270: 1194-1197 (1995).

Riggs et al , "Stable Transformation of Tobacco by Electroporation: Evidence for Plasmid Concatenation," Proc. Natl. Acad. Sci USA 83:5602-5606 (1986).

Rivera et al., "A Humanized System for Pharmacologic Control of Gene Expression," Nature Medicine 2(9): 1028-1032 (1996).

Robertson et al., "DNMT1 Forms a Cokplex With Rb, E2F1 and HDAC1 and Represses Transcription From E2F-Responsive Promoters," Nature Genet. 25:338-342 (2000).

Robyr et al., "Nuclear Hormone Receptor Coregulators in Action: Diversity for Shared Tasks," Mol. Endocrinol. 14:329-347 (2000).

Rogers et al., "Gene Transfer in Plants: Production of Transformed Plants Using Ti Plasmid Vectors," Methods Enzymol. 118:627-641 (1986).

Rollins et al., "Role of TFIIIA Zinc Fingers In Vivo: Analysis of Single-Finger Function in Developing *Xenopus* Embryos," Molecular Cellular Biology 13(8): 4776-4783 (1993).

Sadowski et al., "GAL4-VP16 Is an Unusually Potent Transcriptional Activator," Nature 335: 563-568 (1988).

Saleh et al., "A Novel Zinc Finger Gene on Human Chromosome 1 QTER That Is Alternatively Spliced in Human Tissues and Cell Lines," American Journal of Human Genetics 52: 192-203 (1993).

Sanger et al., "Characteristics of a Strong Promoter From Figwort Mosaic Virus: Comparison With Analogous 35S Promoter From Cauliflower Mosaic Virus and the Regulated Mannopine Synthase Promoter," Plant Mol. Biol. 14:433-443 (1990).

Sap et al., "Repression of Transcription Mediated at a Thyroid Hormone Response Element by the v-erb-a Oncogene Product," Nature 340:242-244 (1989).

Sasaki et al. "A Chloroplast Gene Encoding a Protein With One Zinc Finger," Nuc. Acids. Res. 17(15):6217-6227 (1989).

Schultz et al. "Targeting Histone Deactylase Complexes Via KRAB-Zinc Finger Proteins: The PHD and Bromodomains of KAP-1 Form a Cooperative Unit That Recruits a Novel Isoform of the MI-2A Subunit of NURD," Genes & Develop. 15:428-443 (2000).

Segal et al., "Design of Novel Sequence Specific DNA-Binding Proteins," Curr. Opin. Chem. Biol. 4:34-39 (2000).

Segal et al., "Zinc Fingers and a Green Thumb: Manipulating Gene Expression in Plants," Curr. Opin. Plant Biol. 6:163-168 (2003).

Seipal et al., "Different Activation Domains Stimulates Transcription From Remote ('Enhancer') and Proximal ('Promoter') Positions," EMBO J. 11, 4961-4968 (1992).

Shi et al., "Specific DNA-RNA Hybrid Binding by Zinc Finger Proteins," Science 268: 282-284 (1995).

Shi et al., "DNA Unwinding Induced by Zinc Finger Protein Binding," Biochemistry 35: 3845-3848 (1996).

Shi et al., "A Direct Comparison of the Properties of Natural and Designed Finger Proteins," Chem. & Biol. 2(2): 83-89 (1995).

Shimamoto, "Fertile Transgenic Rice Plants Regenerated From Transformed Protoplasts," Nature 338:274-276 (1989).

Singh et al., "Molecular Cloning of an Enhancer Binding Protein: Isolation by Screening of an Expression Library With a Recognition Site DNA," Cell 52: 415-423 (1988).

Skerka et al., "Coordinate Expression and Distinct DNA-Binding Characteristics of the Four EGR-Zinc Finger Proteins in Jurkat T Lymphocytes," Immunobiology 198: 179-191 (1997).

South et al., "The Nucleocapsid Protein Isolated From HIV-1 Particles Binds Zinc and Forms Retroviral-Type Zinc Fingers," Biochemistry 29: 7786-7789 (1990).

Spengler et al., "Regulation of Apoptosis and Cell Cycle Arrest by ZZC1, a Novel Zinc Finger Protein Expressed in the Pituitary Gland and the Brain," EMBO J. 16(10): 2814-2825 (1997).

Sprenger-Haussels et al., "Transactivation Properties of Parsley Proline-Rich BZIP Transcription Factors," Plant J. 22:1-8 (2000).

Suzuki et al., "Stereochemical Basis of DNA Recognition by Zn Fingers," Nuc. Acids Res. 22(16): 3397-3405 (1994).

Suzuki et al., "DNA Recognition Code of Transcription Factors in the Helix-Turn-Helix, Probe Helix, Hormone Receptor, and Zinc Finger Families," PNAS 91: 12357-12361 (1994).

Swain W F, "Antibodies in Plants," Tibtech 9: 107-109 (1991).

(56) References Cited

OTHER PUBLICATIONS

Swimoff et al, "DNA-Binding Specificity of NGFI-A and Related Zinc Finger Transcription Factors," Mol. Cell. Biol. 15(14): 2275-2287 (1995).
Takamatsu et al., "Expression of Bacterial Chloramphenicol Acetyltransferase Gene in Tobacco Plants Mediated by TMV-RNA," EMBO J. 6:307-311 (1987).
Takatsuji et al., "Target-Sequence Recognition by Separate-Type CYS2/HIS2 Zinc Finger Proteins in Plants," The Journal of Biological Chemistry 271:23368-23373 (1996).
Takatsuji, "A Single Amino Acid Determines the Specificity for the Target Sequence of Two Zinc-Finger Proteins in Plants," Biochem. Biophys. Res. Comm. 224:219-223 (1996).
Takatsuji, "Zinc-Finger Proteins: The Classical Zinc Finger Emerges in Contemporary Plant Science," Plant Mol. Biol. 39:1073-1078 (1999).
Taylor et al., "Designing Zinc-Finger ADRI Mutants With Altered Specificity of DNA Binding To T in UASI Sequences," Biochemistry 34: 3222-3230 (1995).
Thiesen et al., "Amino Acid Substitutions in the SP1 Zinc Finger Domain Alter the DNA Binding Affinity to Cognate SP1 Target Site," Biochem. Biophys. Res. Communications 175(1): 333-338 (1991).
Thiesen et al., "Determination of DNA Binding Specificities of Mutated Zinc Finger Domains," FEBS letters 283(1): 23-26 (1991).
Thiesen H. J. "From Repression Domains to Designer Zinc Finger Proteins: A Novel Strategy for Intracellular Immunization Against HIV," Gene Expression 5: 229-243 (1996).
Thiesen et al., "Multiple Genes Encoding Zinc Finger Domains Are Expressed in Human T Cells," New Biologist 2, 363-374 (1990).
Thukral et al., "Two Monomers of Yeast Transcription Factor ADR1 Bind a Palindromic Sequence Symmetrically to Activate ADH2 Expression," Molecular Cellular Biol. 11(3): 1566-1577 (1991).
Thukral et al., "Localization of a Minimal Binding Domain and Activation Regions in Yeast Regulatory Protein ADR1," Molecular Cellular Biology 9(6): 2360-2369 (1989).
Thukral et al., "Mutations in the Zinc Fingers of ADR1 That Change the Specificity of DNA Binding and Transactivation," Mol. Cell. Biol. 12(6): 2784-2792 (1992).
Thukral et al., "Alanine Scanning Site-Directed Mutagenesis of the Zinc Fingers of Transcription Factor ADR1: Residues That Contact DNA and That Transactivate," PNAS 88: 9188-9192 (1991).
Torchia et al., "Co-Activators and Co-Repressors in the Integration of Transcriptional Responses," Curr. Opin. Cell. Biol. 10:373-383 (1998).
Tyler et al., "The 'Dark Side' of Chromatin Remodeling: Repressive Effects on Transcription," Cell 99:443-446 (1999).
Ulmasov et al., "Activation and Repression of Transcription by Auxin-Response Factors," Proc. Natl. Acad. Sci. USA 96:5844-5849 (1999).
Vortkamp et al., "Identification of Optimized Target Sequences for the GL 13 Zinc Finger Protein," DNA Cell Biol. 14(7): 629-634 (1995).
Wang et al., "Postive and Negative Regulation of Gene Expression in Eukaryotic Cells With an Inducible Transcritional Regulator," Gene Ther. 4:432-441 (1997).
Wang et al., "Dimerization of Zinc Fingers Mediated by Peptides Evolved In Vitro From Random Sequences," PNAS 96: 9568-9573 (1999).
Webster et al., "Conversion of the E1A CYS4 Zinc Finger to a Nonfunctional HIS2, CYS2 Zinc Finger by a Single Point Mutation," PNAS 88: 9989-9993 (1999).
Weissbach & Weissbach, Methods for Plant Molecular Biology, Academic Press, NY, Section VIII, pp. 423-436 (1988).
Whyatt et al., "The Two Zinc Finger-Like Domains of GATA-1 Have Different DNA Binding Specificities," EMBO J. 12(13): 4993-5005 (1993).
Wilson et al., "In Vivo Mutational Analysis of the NGFI-A Zinc Fingers," J. Biol. Chem. 267(6): 3718-3724 (1992).
Witzgall et al., "The Kruppel-Associated Box-A (KRAB-A) Domain of Zinc Finger Proteins Mediates Transcriptional Repression," PNAS 91: 4514-4518 (1994).
Wolfe et al., "DNA Recognition by Cys2His2ZINC Finger Proteins," Annu. Rev. Biophys. Biomol. Struct. 3:183-212 (1999).
Wolfe et al., "Analysis of Zinc Fingers Optimized Via Phage Display: Evaluating the Utility of a Recognition Code," J. Mol. Biol. 285: 1917-1934 (1999).
Wright et al., "Expression of a Zinc Finger Gene in HTLV-I and HTLV-II Transformed Cells," Science 248:588-591 (1990).
Wu et al., "Human Immunodeficiency Virus Type 1 Nucleocapsid Protein Reduces Reverse Transcriptase Pausing at a Secondary Structure Near the Murine Leukemia Virus Polypurine Tract," J. Virol. 70(10): 7132-7142 (1996).
Wu et al., "Functional Analysis of HD2 Histone Deacetylase Homologues in *Arabidopsis thaliana*," Plant J. 22:19-27 (2000).
Wu et al., "Building Zinc Fingers by Selection: Toward a Therapeutic Application," PNAS 92: 344-348 (1995).
Yang et al., "Surface Plasmon Resonance Based Kinetic Studies of Zinc Finger-DNA Interaction," J. Immunol. Methods 183: 175-182 (1995).
Yin and Beachy, "The Regulatory Regiions of the Rice Tungro Baciliform Virus Promoter and Interacting Nuclear Factors in Rice (*Oriza ative* L.)," Plant J. 7:969-980 (1995).
Yu et al., "A Hairpin Ribozyme Inhibits Expression of Diverse Strains of Human Immunodeficiency Virus Type 1," PNAS 90: 6340-6344 (1993).
Zhang et al., "The Mechanism of Action of Thyroid Hormones," Ann Rev Physiol 62:439-466 (2000).
Zhang et al., "Synthetic Zinc Finger Transcription Factor Action at an Endogenous Chromosomal Site. Activation of the Human Erythropoietin Gene," Journal of Biological Chemistry 275(43): 33850-33860 (2000).
Zenke et al., "V-ERBA Specifically Suppresses Transcription of the Avian Erythrocute Anion Transporter (Band 3) Gene," Cell 52:107-119 (1988).
Zenke et al., "V-ERBA Oncogene Activation Entails the Loss of Hormone-Dependant Regulator Activity of C-ERBA," Cell 61:1035-1049 (1990).

* cited by examiner

ZINC FINGER PROTEINS FOR DNA BINDING AND GENE REGULATION IN PLANTS

CROSS REFERENCE TO RELATED APPLICATIONS

This application is a continuation of U.S. patent application Ser. No. 10/055,713 filed Jan. 22, 2002, now U.S. Pat. No. 7,273,923, which claims the benefit under 35 U.S.C. §119(e) of U.S. provisional patent application Ser. No. 60/263,445 filed Jan. 22, 2001 and U.S. provisional patent application Ser. No. 60/290,716 filed May 11, 2001. The disclosures of the aforementioned applications are hereby incorporated by reference in their entireties for all purposes.

TECHNICAL FIELD

The methods and compositions disclosed herein relate generally to the field of regulation of gene expression and specifically to methods of modulating gene expression in plants by utilizing polypeptides derived from plant zinc finger-nucleotide binding proteins.

BACKGROUND

Zinc finger proteins (ZFPs) are proteins that bind to DNA, RNA and/or protein, in a sequence-specific manner, by virtue of a metal stabilized domain known as a zinc finger. See, for example, Miller et al. (1985) *EMBO J.* 4:1609-1614; Rhodes et al. (1993) *Sci. Amer.* February: 56-65; and Klug (1999) *J. Mol. Biol.* 293:215-218. There are at least 2 classes of ZFPs which co-ordinate zinc to form a compact DNA-binding domain. Each class can be distinguished by the identities of the conserved metal-binding amino acids and by the associated architecture of the DNA-binding domain.

The most widely represented class of ZFPs, known as the $C_2H_2$ ZFPs, comprises proteins that are composed of zinc fingers that contain two conserved cysteine residues and two conserved histidine residues. Over 10,000 $C_2H_2$ zinc fingers have been identified in several thousand known or putative transcription factors. Each $C_2H_2$ zinc finger domain comprises a conserved sequence of approximately 30 amino acids that contains the invariant cysteines and histidines in the following arrangement: -Cys-(X)$_{2-4}$-Cys-(X)$_{12}$-His-(X)$_{3-5}$-His (SEQ ID NO: 1). In animal genomes, polynucleotide sequences encoding this conserved amino acid sequence motif are usually found as a series of tandem duplications, leading to the formation of multi-finger domains within a particular transcription factor.

Several structural studies have demonstrated that the conserved $C_2H_2$ amino acid motif folds into a beta turn (containing the two invariant cysteine residues) and an alpha helix (containing the two invariant histidine residues). The alpha helix and beta turn associate along a hydrophobic interface and are held together through the tetrahedral coordination of a zinc atom by the conserved cysteines and histidines.

The three-dimensional structure of a complex between a DNA target site and a polypeptide comprising three $C_2H_2$ zinc fingers derived from the mouse immediate early protein zif268 (also known as Krox-24) has been determined by x-ray crystallography. Pavletich et al. (1991) *Science* 252:809-817. The structure reveals that the amino acid side chains on each zinc finger alpha helix interact specifically with functional groups of the nucleotide bases exposed in the DNA major groove. Each finger interacts with DNA as a module; changes in the sequence of amino acids of the recognition helix can result in corresponding changes in target site specificity. See, for example, Wolfe et al. (1999) *Annu. Rev. Biophys. Biomol. Struct.* 3:183-212.

Another class of ZFPs includes the so-called $C_3H$ ZFPs. See, e.g., Jiang et al. (1996) *J. Biol. Chem.* 271:10723-10730 for a discussion of Cys-Cys-His-Cys ($C_3H$) ZFPs.

The modular nature of sequence-specific interactions between zinc fingers and DNA sequences (i.e., a particular zinc finger of defined sequence binds to a DNA triplet or quadruplet of defined sequence) allows certain DNA-binding domains of predetermined specificity to be designed and/or selected. See, for example, Blackburn (2000) *Curr. Opin. Struct. Biol.* 10:399-400; Segal et al. (2000) *Curr. Opin. Chem. Biol.* 4:34-39. To this end, numerous modifications of animal $C_2H_2$ zinc finger proteins, most often either mouse zif268 or human SP-1, have been reported. See, e.g., U.S. Pat. Nos. 6,007,988; 6,013,453; 6,140,081; 6,140,466; GB Pat. No. 2,348,424; PCT WO98/53057; PCT WO98/53058; PCT WO98/53059; PCT WO98/53060; PCT WO98/54311; PCT WO00/23464; PCT WO 00/42219; Choo et al. (2000) *Curr. Opin. Struct. Biol.* 10:411-416; Segal et al. (2000) supra; and references cited in these publications. The results of these and other studies are generally consistent with the idea that it is possible to obtain $C_2H_2$ ZFPs, based on, for example, the mouse zif268 ZFP or the human SP-1 ZFP, of desired target site specificity. Such target-specific ZFPs are generally obtained by selection or design of individual fingers, each of which has a 3-4 nucleotide target specificity, and assembly of such fingers into a ZFP having a target site specificity of 9-20 nucleotides.

$C_2H_2$ ZFPs have been identified in plants, where they are involved in, for example, developmental regulation of various floral and vegetative organs. See, e.g., Takatsuji (1999) *Plant Mol. Biol.* 39:1073-1078. In plant ZFPs, however, zinc fingers do not generally occur in closely-spaced tandem arrays. For example, in a family of DNA binding proteins identified in *Petunia* (the EPF family), two canonical Cys$_2$-His$_2$ zinc finger motifs are separated by an intervening stretch of between 19 and 232 amino acids. The binding capability of this class of proteins appears to be determined by both the zinc fingers and the intervening amino acids, suggesting that plant zinc finger proteins have a different mechanism of DNA binding that do the zif268 and SP-1 zinc finger proteins, for example. In addition, the sequence specificity of DNA binding by EPF-type plant ZFPs is dependent upon different positions in the recognition helix of the zinc finger than is the specificity of DNA binding by most zif268-type ZFPs. See, for example, Takatsuji (1996) *Biochem. Biophys. Res. Comm.* 224:219-223.

Targeted gene regulation in plants would facilitate numerous applications such as, for example, the optimization of crop traits affecting nutritional value, yield, stress tolerance, pathogen resistance, and resistance to agrochemicals. In addition, targeted gene regulation could be used to study gene function in plants, and to adapt plants for use as biological factories for the production of pharmaceutical compounds or industrial chemicals. Such regulation could theoretically be achieved by design of plant transcriptional regulatory proteins of predetermined DNA sequence specificity. However, to date, naturally occurring plant ZFPs that recognize DNA by using a tandem arrangement of modular zinc finger binding domains (as do zif268 and related ZFPs) have not been described. Therefore, it remains difficult, if not impossible, to design a plant ZFP capable of recognizing and binding to a particular predetermined nucleotide sequence. Furthermore, since the mechanism of DNA binding by plant ZFPs remains largely unknown, no immediate solution to this problem is apparent. Accordingly, the ability to design and/or select plant zinc finger proteins of predetermined target specificity would be desirable.

SUMMARY

The present disclosure provides plant DNA-binding proteins that are modified in such a way that their mechanism and specificity of DNA binding are determined by tandem arrays of modular zinc finger binding units. In this way, design strategies and selection methods which have been developed and utilized for other classes of ZFPs can be applied to the production of plant ZFPs having a predetermined target site specificity, for use in modulation of gene expression in plant cells.

In one aspect, disclosed herein is a modified plant zinc finger protein (ZFP) that binds to a target sequence. The target sequence can be, for example, nucleic acid (DNA or RNA) or amino acids of any length, for instance 3 or more contiguous nucleotides. In certain embodiments, the modified plant ZFP comprises a tandem array of zinc fingers. One, more than one or all of the zinc fingers of the ZFP may be naturally occurring or may be obtained by rational design and/or selection (e.g., phage display, interaction trap, ribosome display and RNA-peptide fusion. Thus, in certain embodiments, one or more of the zinc fingers comprise canonical $C_2H_2$ zinc fingers and in other embodiments, one or more of the zinc fingers comprise non-canonical zinc fingers. In any of the modified plant ZFPs described herein, one or more of the zinc fingers are derived from two or more plant species, for example, by deleting and/or substituting one or more amino acid residues as compared to a naturally occurring plant ZFP. In certain embodiments, one or more amino acid residues are deleted between one or more of the zinc fingers.

Thus, in one embodiment, plant zinc finger proteins (ZFPs) are modified, for example, by deletion of inter-zinc finger sequences and/or insertion of additional zinc finger sequences, to generate one or more tandem arrays of zinc fingers. Thus, in contrast to naturally occurring plant zinc finger proteins, their mechanism and specificity of DNA binding are determined by tandem arrays of modular zinc finger binding units. In another embodiment, plant zinc fingers of disparate origin (e.g., zinc fingers from *Petunia* and *Arabidopsis*) are recombined into a tandem array of modular zinc finger binding units.

In yet another aspect, a fusion polypeptide comprising (i) a modified plant ZFP as described herein and (ii) at least one functional domain are described. The functional domain may be a repressive domain or an activation domain.

In yet another aspect, isolated polynucleotides encoding any of the modified plant zinc finger proteins or fusion polypeptides described herein are provided. Also provided are expression vectors comprising these polynucleotides. Also described are host cell comprising these polynucleotides and/or expression vectors.

In another aspect, a method for modulating gene expression in a plant cell comprising contacting the cell with any of the modified plant ZFPs described herein is provided. In one embodiment, the protein comprising a tandem array of zinc fingers is provided. Preferably, the protein is expressed in the cell, for example, by introducing the protein and/or a nucleic acid encoding the protein into the cell. In certain embodiments, the zinc fingers of the protein comprise an adapted amino acid sequence at any one or more of residues −1 through +6 of the recognition helix. The adapted amino acid sequence can be obtained by rational design and/or by selection (e.g., using methods such as phage display, interaction trap, ribosome display, RNA-peptide fusion or combinations of one or more of these methods). In certain embodiments, the protein comprises zinc finger backbones from different species, for example different plant species. In other embodiments, the protein comprises zinc finger backbones of plant origin, fungal origin or combinations thereof.

Furthermore, in certain embodiments, the protein is obtained by deletion of inter-finger sequences from a plant ZFP.

In other aspects, the methods described herein make use of a fusion protein comprising a tandem array of zinc fingers and one or more functional domains, for example, one or more transcriptional activation (e.g., C1, etc.) or repression domains.

In other aspects, the compositions and methods described herein find use in a variety of applications in which modulation of gene expression alters the phenotype and/or composition of the plant or plant cell, for example by optimizing crop traits such as nutritional value, yield, stress tolerance, pathogen resistance, resistance to agrochemicals (e.g., insecticides and/or herbicides) and the like; and by adapting plants for use in production of pharmaceutical compounds and/or industrial chemicals. In certain embodiments, the modulation of gene expression can be used to study genetic pathways and/or gene functions in plants.

These and other embodiments will readily occur to those of skill in the art in light of the disclosure herein.

DETAILED DESCRIPTION

General

Figure 1A:
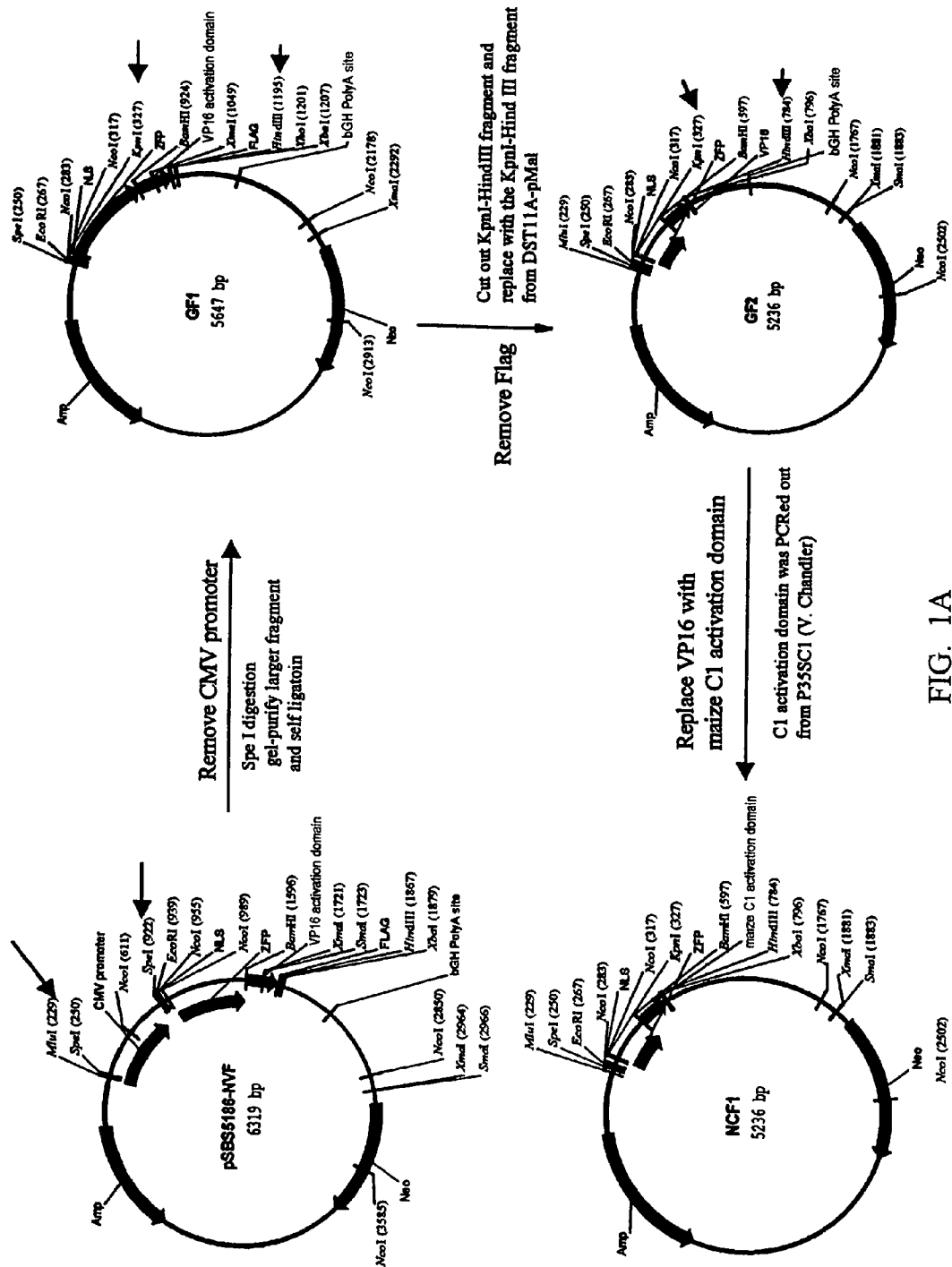
FIG. 1 is a schematic depicting construction of the YCF3 expression vector useful in expressing modified plant ZFPs.

The present disclosure provides modified plant ZFPs (and functional fragments thereof), wherein zinc fingers are arranged in one or more tandem arrays such that, upon DNA binding, each zinc finger contacts a triplet or quadruplet target subsite. In preferred embodiments, the target subsites are contiguous to one another. The modified plant ZFP can be a fusion polypeptide and, either by itself or as part of such a fusion, can enhance or suppress expression of a gene (i.e., modulate gene expression). Polynucleotides encoding modified plant ZFPs, and polynucleotides encoding fusion proteins comprising one or more modified plant ZFPs are also provided. Additionally provided are compositions comprising, in combination with an acceptable carrier, any of the modified plant zinc finger binding polypeptides described herein or functional fragments thereof; and compositions comprising a nucleotide sequence that encodes a modified plant zinc finger binding polypeptide or functional fragment thereof, wherein the modified plant zinc finger polypeptide or functional fragment thereof binds to a cellular nucleotide sequence to modulate the function of the cellular nucleotide sequence.

Currently, ZFPs targeted to specific predetermined sequences are derived from non-plant ZFPs such as *Xenopus*

TFIIIA, murine zif268, human SP-1 and the like. Accordingly, in one embodiment, modified plant zinc finger proteins, targeted to predetermined sequences, are described wherein all or substantially all of the sequences making up the ZFP are derived from one or more plant sources. Furthermore, the modified plant ZFPs are organized in non-plant ZFP structures, for example structures in which individual zinc fingers (e.g., $C_2H_2$ fingers) are linked by short linker sequences, or structures that do not contain native plant DNA binding sequences such as inter-zinc finger sequences of a plant zinc finger protein, (which can be generated from plant ZFPs, for example, by deletion of inter-zinc finger amino acid sequences). In certain embodiments, all amino acid residues of a modified plant ZFP are derived from a non-modified plant ZFP (e.g., when a modified plant ZFP is obtained by deletion of inter-finger sequences from a non-modified plant ZFP). In other embodiments, one or more amino acid residues of a modified plant ZFP (e.g., amino acids involved in sequence-specific and/or non-specific DNA contacts) can be either designed or selected, and thus may not constitute part of the original plant ZFP sequence.

It is preferred that a modified plant zinc finger protein be a multi-finger protein, for example comprising at least three zinc-coordinating fingers. In the standard nomenclature for ZFPs, the "first" finger is the N-terminal-most finger of the protein (with respect to the other fingers) and binds to the 3'-most triplet (or quadruplet) subsite in the target site. Additional fingers, moving towards the C-terminus of the protein, are numbered sequentially.

In other embodiments, one or more of the component fingers of the modified plant ZFP will be a non-$C_2H_2$ structure. For example, in certain embodiments, a three-finger zinc finger protein is provided wherein the first two fingers are of the $C_2H_2$ class but the third finger is non-$C_2H_2$ (e.g., $C_3H$ or other structure) as described, for example, in International Publication WO 02/57293.

Therefore, the modified plant ZFPs disclosed herein differ from previously described designed zinc finger protein transcription factors in that they are entirely or primarily composed of plant sequences. Nonetheless, the plant sequences are assembled such that the overall structure of the binding region of the modified plant protein is similar to that of a non-plant eukaryotic zinc finger. Thus, modified plant ZFPs, as disclosed herein, comprise plant sequences either for the entire ZFP or for most of the ZFP. In the latter case, plant sequences are used preferably in all regions except those residues involved in recognition and/or binding to the target site, which can comprise, for example, sequences obtained by rational design and/or selection.

It will be readily apparent that various combinations of zinc fingers can be used in a single modified plant ZFP. For example, all of the finger components can be designed (i.e., their sequences are obtained as a result of rational design methods); all of the finger components can be selected (i.e., their sequences are obtained by a selection method such as, e.g. phage display, two-hybrid systems or interaction trap assays); all of the finger components can be naturally-occurring plant zinc fingers; or the component fingers of a modified plant ZFP can be any combination of naturally-occurring plant zinc fingers, designed fingers and selected fingers.

In additional embodiments, the modified plant zinc finger proteins described herein (and/or functional fragments thereof) are used in fusion proteins, for example fusions of a modified plant ZFP DNA-binding domain with, e.g., a repression domain, an activation domain, a chromatin remodeling domain, a component of a chromatin remodeling complex, a methyl-binding domain, a methyltransferase, an insulator-binding protein, and/or functional fragments thereof. Polynucleotides encoding any of the zinc finger proteins, components thereof, functional fragments thereof, and fusions thereof are also provided.

In additional embodiments, methods for modulating gene expression in plant cells, using modified plant ZFPs are provided. Because naturally-occurring plant ZFPs, which modulate plant gene expression in vivo, do not contain zinc fingers in tandem arrays, the ability of a ZFP containing a tandem array of zinc fingers to modulate gene expression in a plant cell is a surprising discovery. Thus, the compositions and methods disclosed herein allow the insights gained from work with non-plant ZFPs such as zif268 and Sp-1 to be applied to regulation of plant gene expression by plant proteins; so that targeted regulation of gene expression in plant cells can be achieved by mechanisms similar to those already described for animal cells. In addition, by allowing targeted regulation of plant gene expression by plant proteins, the present methods and compositions will help to allay potential concerns regarding the introduction of animal proteins into plants.

The practice of the disclosed methods employs, unless otherwise indicated, conventional techniques in molecular biology, biochemistry, genetics, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989; Ausubel et al., CURRENT PROTOCOLS IN MOLECULAR BIOLOGY, John Wiley & Sons, New York, 1987 and periodic updates; and the series METHODS IN ENZYMOLOGY, Academic Press, San Diego.

The disclosures of all patents, patent applications and publications mentioned herein are hereby incorporated by reference in their entireties.

DEFINITIONS

The terms "nucleic acid," "polynucleotide," and "oligonucleotide" are used interchangeably and refer to a deoxyribonucleotide or ribonucleotide polymer in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally occurring amino acid, for example selenocysteine (Bock et al. (1991) *Trends Biochem. Sci.* 16:463-467; Nasim et al. (2000) *J. Biol. Chem.* 275:14, 846-14,852) and the like.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity. A "binding profile" refers to a plurality of target sequences that are recognized and bound by a particular binding protein. For example, a binding profile can be determined by contacting a binding protein with a population of randomized target sequences to identify a sub-population of target sequences bound by that particular binding protein.

A "zinc finger binding protein" is a protein or segment within a larger protein that binds DNA, RNA and/or protein in a sequence-specific manner as a result of stabilization of protein structure through coordination of a zinc ion. The term zinc finger binding protein is often abbreviated as zinc finger protein or ZFP.

A zinc finger "backbone" is the portion of a zinc finger outside the region involved in DNA major groove interactions; i.e., the regions of the zinc finger outside of residues −1 through +6 of the alpha helix. The backbone comprises the beta strands, the connecting region between the second beta strand and the alpha helix, the portion of the alpha helix distal to the first conserved histidine residue, and the inter-finger linker sequence(s). Thus, a plant zinc finger "backbone" refers to sequences derived from one or more plant ZFPs, where these sequences are not naturally involved in DNA major groove interactions.

As used herein, the term "modified plant" zinc finger protein refers to a zinc finger protein comprising plant ZFP sequences organized in a non-plant ZFP structure, for example to eliminate the long stretches of amino acid sequence between zinc fingers found in many naturally-occurring plant ZFPs. Thus, all, most or some of the sequences in the zinc finger regions of a modified plant ZFP may be derived from a plant. Additionally, modified plant ZFPs in these non-plant structures can further include one or more residues or regions (e.g., fingers) of non-plant origin, such as, for example, naturally-occurring fingers or fingers as may be obtained by design or selection, so long as DNA binding capability is maintained.

A "non-canonical" zinc finger protein is a protein not occurring in nature that has been designed and/or selected so as to differ from the canonical binding domain consensus sequence Cys-Cys-His-His (e.g., Cys2-His2). Thus, non-canonical zinc finger proteins comprise a substitution, addition and/or deletion of at least one amino acid, compared to a naturally occurring zinc finger protein. Non-limiting examples of non-canonical zinc fingers include binding domains comprising Cys-Cys-His-Cys (e.g., C3H) sequences and the like. (See, also International Publication WO 02/57293).

A "designed" zinc finger protein is a protein not occurring in nature whose structure and composition results principally from rational criteria. Criteria for rational design include application of substitution rules and computerized algorithms for processing information in a database storing information of existing ZFP designs and binding data, for example as described in co-owned PCT WO 00/42219. A "selected" zinc finger protein is a protein not found in nature whose production results primarily from an empirical process such as phage display, two-hybrid systems and/or interaction trap assays. See e.g., U.S. Pat. No. 5,789,538; U.S. Pat. No. 6,007,988; U.S. Pat. No. 6,013,453; WO 95/19431; WO 96/06166; WO 98/54311 and Joung et al. (2000) *Proc. Natl. Acad. Sci. USA* 97:7382-7387. Selection methods also include ribosome display systems (e.g., PCT WO 00/27878) and mRNA-peptide fusion systems (e.g., U.S. Pat. No. 6,207,446; PCT WO 00/47775). Amino acid sequences of polypeptides (e.g., zinc fingers) obtained by selection or design are referred to as "adapted" amino acid sequences. Designed and/or selected ZFPs are modified according to the methods and compositions disclosed herein and may also be referred to as "engineered" ZFPs.

The term "naturally-occurring" is used to describe an object that can be found in nature, as distinct from being artificially produced by a human. For example, naturally occurring plant ZFPs are characterized by long spacers of diverse lengths between adjacent zinc finger components.

Nucleic acid or amino acid sequences are "operably linked" (or "operatively linked") when placed into a functional relationship with one another. For instance, a promoter or enhancer is operably linked to a coding sequence if it regulates, or contributes to the modulation of, the transcription of the coding sequence. Operably linked DNA sequences are typically contiguous, and operably linked amino acid sequences are typically contiguous and in the same reading frame. However, since enhancers generally function when separated from the promoter by up to several kilobases or more and intronic sequences may be of variable lengths, some polynucleotide elements may be operably linked but not contiguous. Similarly, certain amino acid sequences that are non-contiguous in a primary polypeptide sequence may nonetheless be operably linked due to, for example folding of a polypeptide chain.

With respect to fusion polypeptides, the term "operatively linked" can refer to the fact that each of the components performs the same function in linkage to the other component as it would if it were not so linked. For example, with respect to a fusion polypeptide in which a modified plant ZFP DNA-binding domain is fused to a functional domain (or functional fragment thereof), the ZFP DNA-binding domain and the functional domain (or functional fragment thereof) are in operative linkage if, in the fusion polypeptide, the modified plant ZFP DNA-binding domain portion is able to bind its target site and/or its binding site, while the functional domain (or functional fragment thereof) is able to modulate (e.g., activate or repress) transcription.

"Specific binding" between, for example, a ZFP and a specific target site means a binding affinity of at least $1 \times 10^6$ $M^{-1}$.

A "fusion molecule" is a molecule in which two or more subunit molecules are linked, preferably covalently. The subunit molecules can be the same chemical type of molecule, or can be different chemical types of molecules. Examples of the first type of fusion molecule include, but are not limited to, fusion polypeptides (for example, a fusion between a modified plant ZFP DNA-binding domain and a functional domain) and fusion nucleic acids (for example, a nucleic acid encoding the fusion polypeptide described herein). Examples of the second type of fusion molecule include, but are not limited to, a fusion between a triplex-forming nucleic acid and a polypeptide, and a fusion between a minor groove binder and a nucleic acid.

A "gene," for the purposes of the present disclosure, includes a DNA region encoding a gene product (see below), as well as all DNA regions that regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. Further, a promoter can be a normal cellular promoter or, for example, a promoter of an infecting microorganism such as, for example, a bacterium or a virus.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" and "augmentation of gene expression" refer to any process that results in an increase in production of a gene product. A gene product can be either RNA (including, but not limited to, mRNA, rRNA, tRNA, and structural RNA) or protein. Accordingly, gene activation includes those processes that increase transcription of a gene and/or translation of an mRNA. Examples of gene activation processes which increase transcription include, but are not limited to, those which facilitate formation of a transcription initiation complex, those which increase transcription initiation rate, those which increase transcription elongation rate, those which increase processivity of transcription and those which relieve transcriptional repression (by, for example, blocking the binding of a transcriptional repressor). Gene activation can constitute, for example, inhibition of repression as well as stimulation of expression above an existing level. Examples of gene activation processes that increase translation include those that increase translational initiation, those that increase translational elongation and those that increase mRNA stability. In general, gene activation comprises any detectable increase in the production of a gene product, preferably an increase in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more.

"Gene repression" and "inhibition of gene expression" refer to any process that results in a decrease in production of a gene product. A gene product can be either RNA (including, but not limited to, mRNA, rRNA, tRNA, and structural RNA) or protein. Accordingly, gene repression includes those processes that decrease transcription of a gene and/or translation of an mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes that decrease translation include those that decrease translational initiation, those that decrease translational elongation and those that decrease mRNA stability. Transcriptional repression includes both reversible and irreversible inactivation of gene transcription. In general, gene repression comprises any detectable decrease in the production of a gene product, preferably a decrease in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more. Most preferably, gene repression results in complete inhibition of gene expression, such that no gene product is detectable.

The term "modulate" refers to a change in the quantity, degree or extent of a function. For example, the modified plant zinc finger-nucleotide binding polypeptides disclosed herein can modulate the activity of a promoter sequence by binding to a motif within the promoter, thereby inducing, enhancing or suppressing transcription of a gene operatively linked to the promoter sequence. Alternatively, modulation may include inhibition of transcription of a gene wherein the modified zinc finger-nucleotide binding polypeptide binds to the structural gene and blocks DNA dependent RNA polymerase from reading through the gene, thus inhibiting transcription of the gene. The structural gene may be a normal cellular gene or an oncogene, for example. Alternatively, modulation may include inhibition of translation of a transcript. Thus, "modulation" of gene expression includes both gene activation and gene repression.

Modulation can be assayed by determining any parameter that is indirectly or directly affected by the expression of the target gene. Such parameters include, e.g., changes in RNA or protein levels; changes in protein activity; changes in product levels; changes in downstream gene expression; changes in transcription or activity of reporter genes such as, for example, luciferase, CAT, beta-galactosidase, or GFP (see, e.g., Mistili & Spector, (1997) *Nature Biotechnology* 15:961-964); changes in signal transduction; changes in phosphorylation and dephosphorylation; changes in receptor-ligand interactions; changes in concentrations of second messengers such as, for example, cGMP, cAMP, $IP_3$, and $Ca^{2+}$; changes in cell growth, changes in chemical composition (e.g., nutritional value), and/or changes in any functional effect of gene expression. Measurements can be made in vitro, in vivo, and/or ex vivo. Such functional effects can be measured by conventional methods, e.g., measurement of RNA or protein levels, measurement of RNA stability, and/or identification of downstream or reporter gene expression. Readout can be by way of, for example, chemiluminescence, fluorescence, colorimetric reactions, antibody binding, inducible markers, ligand binding assays; changes in intracellular second messengers such as cGMP and inositol triphosphate ($IP_3$); changes in intracellular calcium levels; cytokine release, and the like.

"Eucaryotic cells" include, but are not limited to, fungal cells (such as yeast), plant cells, animal cells, mammalian cells and human cells. Similarly, "prokaryotic cells" include, but are not limited to, bacteria.

A "regulatory domain" or "functional domain" refers to a protein or a polypeptide sequence that has transcriptional modulation activity, or that is capable of interacting with proteins and/or protein domains that have transcriptional modulation activity. Typically, a functional domain is covalently or non-covalently linked to a ZFP to modulate transcription of a gene of interest. Alternatively, a ZFP can act, in the absence of a functional domain, to modulate transcription. Furthermore, transcription of a gene of interest can be modulated by a ZFP linked to multiple functional domains.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well known in the art. Similarly, methods for determining protein function are well known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340: 245-246; U.S. Pat. No. 5,585,245 and PCT WO 98/44350.

A "target site" or "target sequence" is a sequence that is bound by a binding protein such as, for example, a ZFP. Target sequences can be nucleotide sequences (either DNA or RNA) or amino acid sequences. By way of example, a DNA target sequence for a three-finger ZFP is generally either 9 or 10 nucleotides in length, depending upon the presence and/or nature of cross-strand interactions between the ZFP and the target sequence. Target sequences can be found in any DNA or RNA sequence, including regulatory sequences, exons, introns, or any non-coding sequence.

A "target subsite" or "subsite" is the portion of a DNA target site that is bound by a single zinc finger, excluding cross-strand interactions. Thus, in the absence of cross-strand interactions, a subsite is generally three nucleotides in length. In cases in which a cross-strand interaction occurs (e.g., a "D-able subsite," as described for example in co-owned PCT WO 00/42219, incorporated by reference in its entirety herein) a subsite is four nucleotides in length and overlaps with another 3- or 4-nucleotide subsite.

The term "effective amount" includes that amount which results in the desired result, for example, deactivation of a previously activated gene, activation of a previously repressed gene, or inhibition of transcription of a structural gene or translation of RNA.

Zinc Finger Proteins

Zinc finger proteins are polypeptides that comprise zinc finger components. For example, zinc finger proteins can have one to thirty-seven fingers, commonly having 2, 3, 4, 5 or 6 fingers. Zinc finger DNA-binding proteins are described, for example, in Miller et al. (1985) *EMBO J.* 4:1609-1614; Rhodes et al. (1993) *Scientific American* February: 56-65; and Klug (1999) *J. Mol. Biol.* 293:215-218. A zinc finger protein recognizes and binds to a target site (sometimes referred to as a target sequence or target segment) that represents a relatively small portion of sequence within a target gene. Each component finger of a zinc finger protein binds to a subsite within the target site. The subsite includes a triplet of three contiguous bases on the same strand (sometimes referred to as the target strand). The three bases in the subsite can be individually denoted the 5' base, the mid base, and the 3' base of the triplet, respectively. The subsite may or may not also include a fourth base on the non-target strand that is the complement of the base immediately 3' of the three contiguous bases on the target strand. The base immediately 3' of the three contiguous bases on the target strand is sometimes referred to as the 3' of the 3' base. Alternatively, the four bases of the target strand in a four base subsite can be numbered 4, 3, 2, and 1, respectively, starting from the 5' base.

Zinc finger proteins have been identified in a variety of species. While plant ZFPs are characterized by long spacers between fingers, non-plant ZFPs have much shorter linkers between-finger regions. An exemplary non-plant ZFP is the human transcription factor, Sp-1. As described in detail in WO 00/42219, each of the three zinc fingers in Sp-1 is approximately 30 amino acids in length and is made up of a beta turn (approximately 12 residues in length), and alpha helix (approximately 10-12 residues in length) and short sequence connecting between the beta turn and the alpha helix of approximately 2 residues and an inter-finger linker sequence of 4-5 residues. Exemplary sequences of the zinc fingers of Sp-1 are shown in co-owned WO 00/42219. Also disclosed in WO 00/42219 is an SP-1 consensus sequence, as described by Berg (1992) *Proc. Natl. Acad. Sci. USA* 89:11, 109-11,110, which is useful in the design of targeted zinc finger proteins.

Furthermore, in discussing the specificity-determining regions of a zinc finger, amino acid +1 refers to the first amino acid in the alpha-helical portion of the zinc finger. The portion of a zinc finger that is generally believed to be responsible for its binding specificity lies between −1 and +6. Amino acid ++2 refers to the amino acid at position +2 in a second zinc finger adjacent (in the C-terminal direction) to the zinc finger under consideration. In certain circumstances, a zinc finger binds to its triplet subsite substantially independently of other fingers in the same zinc finger protein. Accordingly, the binding specificity of a zinc finger protein containing multiple fingers is, to a first approximation, the aggregate of the specificities of its component fingers. For example, if a zinc finger protein is formed from first, second and third fingers that individually bind to triplets XXX, YYY, and ZZZ, the binding specificity of the zinc finger protein is 3'-XXX YYY ZZZ-5'.

The relative order of fingers in a zinc finger protein, from N-terminal to C-terminal, determines the relative order of triplets in the target sequence, in the 3' to 5' direction that will be recognized by the fingers. For example, if a zinc finger protein comprises, from N-terminal to C-terminal, first, second and third fingers that individually bind to the triplets 5'-GAC-3',5'-GTA-3' and 5'-GGC-3', respectively, then the zinc finger protein binds to the target sequence 5'-GGCGTA-GAC-3' (SEQ ID NO: 2). If the zinc finger protein comprises the fingers in another order, for example, second finger, first finger, third finger, then the zinc finger protein binds to a target segment comprising a different permutation of triplets, in this example, 5'-GGCGACGTA-3' (SEQ ID NO: 3). See Berg et al. (1996) *Science* 271:1081-1086. The numbering convention used above is standard in the field for the region of a zinc finger conferring binding specificity. The amino acid on the N-terminal side of the first invariant His residue is assigned the number +6, and other amino acids, proceeding in an N-terminal direction, are assigned successively decreasing numbers. The alpha helix generally begins at residue +1 and extends to the residue following the second conserved histidine. The entire helix can therefore be of variable length, e.g., between 11 and 13 residues.

A. Modified Plant ZFPs

A modified plant zinc finger protein is an amino acid sequence, or variant or fragment thereof, which is capable of binding to a target sequence and which comprises sequences derived from plant sources which have been reassembled in a non-plant ZFP structure. Thus, one or more of the following regions of a modified plant zinc finger are derived from one or more plant sources: the first beta strand, the second beta strand, the alpha helix, and the linker.

It is to be understood that "non-plant" structure refers to any structure that deviates from typical naturally occurring plant ZFPs. One example of a non-plant ZFP scaffold suitable for providing a template for assembling plant-derived sequences is one in which the number of residues between the second histidine of one finger and the first cysteine of the adjacent, C-terminal finger is relatively short. In contrast to typical non-plant ZFPs, plant ZFPs are characterized by long spacers between adjacent fingers. Thus, in certain embodiments, a non-plant structure refers to ZFPs which contain tandem arrays of zinc fingers, i.e., structures in which there are between 5 and 50 amino acids between fingers, more preferably between 5 and 25 amino acids and even more preferably between 5 and 20 amino acids, or any integer therebetween.

Thus, in certain embodiments, the modified plant ZFPs disclosed herein will not contain the sequence QALGGH (SEQ ID NO: 105) in the recognition region, which is highly conserved in many plant ZFPs. See Takatsuji, (1999) *Plant Mol. Biol.* 39:1073-1078 and references cited therein. Yet another example of a non-plant ZFP structure is one that comprises both canonical $C_2H_2$ fingers and non-canonical (e.g., non-$C_2H_2$) fingers. (See, also International Publication WO 02/57293). Other examples of non-plant structures can be readily determined by those of skill in the art in view of the teachings herein. Furthermore, it is to be understood that the modified plant ZFPs described herein may have one or more of these non-plant organization characteristics.

Thus, although the modified plant ZFPs disclosed herein are composed wholly or partly of plant sequences, they have a non-plant structure. The non-plant structure of the modified plant ZFP can be similar to that of any class of non-plant ZFP, for instance the $C_2H_2$ canonical class of ZFPs as exemplified by TFIIIA, Zif268 and Sp-1. Furthermore, the modified plant ZFP can comprise sequences from more than one class of ZFP, and selecting particular DNA binding residues and plant backbone residues to achieve the desired effector functions is within the ordinary skill in the art. The Sp-1 sequence used for construction of targeted zinc finger proteins corresponds to amino acids 531 to 624 in the Sp-1 transcription factor. Thus, models for design of modified plant ZFPs include, but are not limited to, Sp-1 and an Sp-1 consensus sequence, described by Berg (1992) *Proc. Natl. Acad. Sci. USA* 89:11,109-11,110 and by Shi et al. (1995) *Chemistry and Biology* 1:83-89. The amino acid sequences of these ZFP frameworks are disclosed in co-owned PCT WO 00/42219, the disclosure of which is incorporated by reference. Fungal ZFPs can also be used as models for design and/or as sources of zinc finger sequences for modified plant ZFPs. See, e.g., WO 96/32475. Other suitable ZFPs are known to those of skill in the art and are described herein. The documents cited herein also disclose methods of assessing binding specificity of modified ZFPs.

Optionally, modified plant ZFPs can include one or more residues not present in a naturally occurring plant zinc finger such as can be obtained by, for example, design and/or selection. For example, one or more sequence in the alpha-helical region, particularly residues involved in target-recognition (e.g., amino acids −1, +2, +3 and +6), can be altered with respect to a naturally occurring plant ZFP. Any recognition sequence can be chosen, for example, by selecting residues known to bind to certain target sequences, determined as described herein and in the references cited herein.

Sequences from any ZFP that is used in the methods described herein can be altered by mutagenesis, substitution, insertion and/or deletion of one or more residues so that the non-recognition plant-derived residues do not correspond exactly to the zinc finger from which they are derived. Preferably, at least 75% of the modified plant ZFP residues will correspond to those of the plant sequences, more often 90%, and most preferably greater than 95%.

In general, modified plant ZFPs are produced by a process of analysis of plant sequences, for example those sequences that are publicly available on any number of databases. Three-dimensional modeling can be used, but is not required. Typically, plant sequences are selected for their homology to non-plant ZFPs, for example, by selecting plant ZFPs that most closely resemble the chosen non-plant ZFP scaffold (e.g., a $C_3H$ structures and/or $C_2H_2$ ZFP structure such as Sp-1 or Sp-1 consensus) and binding mode. The plant sequences are then assembled in a non-plant binding mode structure, for instance as three zinc fingers separated by short linkers, as are present in non-plant ZFPs. Thus, the process of obtaining a modified plant ZFP with a predetermined binding specificity can begin by analysis of naturally occurring plant ZFPs.

Once selected plant sequences have been organized and assembled to reflect a non-plant structure, alterations in the recognition residues (i.e., positions −1 to +6 of the alpha helix) can be made so as to confer a desired binding specificity, for example as described in co-owned WO 00/42219; WO 00/41566; as well as U.S. Pat. Nos. 5,789,538; 6,007,408; 6,013,453; 6,140,081 and 6,140,466; and PCT publications WO 95/19431, WO 98/54311, WO 00/23464; WO 00/27878; WO98/53057; WO98/53058; WO98/53059; and WO98/53060.

In other embodiments, one or more residues, for example recognition residues, can be derived from non-plant sources and inserted into the modified plant ZFP structure. In particular, non-plant sequences that have previously been shown to bind to specific target sequences can be incorporated into the modified plant ZFP to provide the desired binding specificity. Thus, the modified plant ZFPs can include, one or more non-plant derived residues involved in DNA binding where these binding residues have been designed and/or selected to recognize a particular target site, for example as described.

In certain embodiments, modified plant ZFPs, as disclosed herein, contain additional modifications in their zinc fingers, for example, as described in applications of which the benefit is claimed herein. Such additional modifications include, for example, substitution of a zinc-coordinating amino acid residue (i.e., cysteine and/or histidine) with a different amino acid. A modified ZFP of this type can include any number of zinc finger components, and, in one embodiment, contains three zinc fingers. Typically, the C-terminal-most (e.g., third) finger of the ZFP is substituted in one or more zinc-coordinating residues. The other fingers of the protein can be naturally occurring zinc finger components, modified plant components, canonical $C_2H_2$ fingers or combinations of these components.

Also included herein are nucleic acids encoding a ZFP comprising at least one modified plant zinc finger as described herein.

B. Linkage

Two or more zinc finger proteins can be linked to have a target site specificity that is, to a first approximation, the aggregate of that of the component zinc finger proteins. For example, a first modified plant zinc finger protein having first, second and third component fingers that respectively bind to XXX, YYY and ZZZ can be linked to a second modified plant zinc finger protein having first, second and third component fingers with binding specificities, AAA, BBB and CCC. The binding specificity of the combined first and second proteins is thus 5'-CCCBBBAAANZZZYYYXXX-3' (SEQ ID NO:4), where N indicates a short intervening region (typically 0-5 bases of any type). In this situation, the target site can be viewed as comprising two target segments separated by an intervening segment.

Linkage of zinc fingers and zinc finger proteins can be accomplished using any of the following peptide linkers:

```
TGEKP Liu et al. (1997) Proc. Natl.
Acad. Sci. USA 94: 5525-5530.

(G4S)n Kim et al. (1996) Proc. Natl.    (SEQ ID NO: 6)
Acad. Sci. USA 93: 1156-1160.

GGRRGGGS                                 (SEQ ID NO: 7)

LRQRDGERP                                (SEQ ID NO: 8)

LRQKDGGGSERP                             (SEQ ID NO: 9)

LRQKD(G3S)2ERP.                          (SEQ ID NO: 10)
```

Alternatively, flexible linkers can be rationally designed using computer programs capable of modeling both DNA-binding sites and the peptides themselves, or by phage display methods. In a further variation, non-covalent linkage can be achieved by fusing two zinc finger proteins with domains promoting heterodimer formation of the two zinc finger proteins. For example, one zinc finger protein can be fused with fos and the other with jun (see Barbas et al., WO 95/119431). Alternatively, dimerization interfaces can be obtained by selection. See, for example, Wang et al. (1999) Proc. Natl. Acad. Sci. USA 96:9568-9573.

C. Fusion Molecules

The modified plant zinc finger proteins described herein can also be used in the design of fusion molecules that facilitate regulation of gene expression, particularly in plants. Thus, in certain embodiments, the compositions and methods disclosed herein involve fusions between at least one of the zinc finger proteins described herein (or functional fragments thereof) and one or more functional domains (or functional fragments thereof), or a polynucleotide encoding such a fusion. The presence of such a fusion molecule in a cell allows a functional domain to be brought into proximity with a sequence in a gene that is bound by the zinc finger portion of the fusion molecule. The transcriptional regulatory function of the functional domain is then able to act on the gene, by, for example, modulating expression of the gene.

In certain embodiments, fusion proteins comprising a modified plant zinc finger DNA-binding domain and a functional domain are used for modulation of endogenous gene expression as described, for example, in co-owned PCT WO 00/41566. Modulation includes repression and activation of gene expression; the nature of the modulation generally depending on the type of functional domain present in the fusion protein. Any polypeptide sequence or domain capable of influencing gene expression (or functional fragment thereof) that can be fused to a DNA-binding domain, is suitable for use.

An exemplary functional domain for fusing with a ZFP DNA-binding domain, to be used for repressing gene expression, is a KRAB repression domain from the human KOX-1 protein (see, e.g., Thiesen et al., New Biologist 2, 363-374 (1990); Margolin et al., Proc. Natl. Acad. Sci. USA 91, 4509-4513 (1994); Pengue et al., Nucl. Acids Res. 22:2908-2914 (1994); Witzgall et al., Proc. Natl. Acad. Sci. USA 91, 4514-4518 (1994). Another suitable repression domain is methyl binding domain protein 2B (MBD-2B) (see, also Hendrich et al. (1999) Mamm Genome 10:906-912 for description of MBD proteins). Another useful repression domain is that associated with the v-ErbA protein. See, for example, Damm, et al. (1989) Nature 339:593-597; Evans (1989) Int. J. Cancer Suppl. 4:26-28; Pain et al. (1990) New Biol. 2:284-294; Sap et al. (1989) Nature 340:242-244; Zenke et al. (1988) Cell 52:107-119; and Zenke et al. (1990) Cell 61:1035-1049.

Additional exemplary repression domains include, but are not limited to, thyroid hormone receptor (TR), SID, MBD1, MBD2, MBD3, MBD4, MBD-like proteins, members of the DNMT family (e.g., DNMT1, DNMT3A, DNMT3B), Rb, MeCP1 and MeCP2. See, for example, Zhang et al. (2000) Ann Rev Physiol 62:439-466; Bird et al. (1999) Cell 99:451-454; Tyler et al. (1999) Cell 99:443-446; Knoepfler et al. (1999) Cell 99:447-450; and Robertson et al. (2000) Nature Genet. 25:338-342. Additional exemplary repression domains include, but are not limited to, ROM2 and AtHD2A. See, for example, Chern et al. (1996) Plant Cell 8:305-321; and Wu et al. (2000) Plant J. 22:19-27.

Suitable domains for achieving activation include the HSV VP16 activation domain (see, e.g., Hagmann et al., J. Virol. 71, 5952-5962 (1997)) nuclear hormone receptors (see, e.g., Torchia et al., Curr. Opin. Cell. Biol. 10:373-383 (1998)); the p65 subunit of nuclear factor kappa B (Bitko & Barik, J. Virol. 72:5610-5618 (1998) and Doyle & Hunt, Neuroreport 8:2937-2942 (1997)); Liu et al., Cancer Gene Ther. 5:3-28 (1998)), or artificial chimeric functional domains such as VP64 (Seifpal et al., EMBO J. 11, 4961-4968 (1992)).

Additional exemplary activation domains include, but are not limited to, p300, CBP, PCAF,SRC1 PvALF, and ERF-2. See, for example, Robyr et al. (2000) Mol. Endocrinol. 14:329-347; Collingwood et al. (1999) J. Mol. Endocrinol. 23:255-275; Leo et al. (2000) Gene 245: 1-11; Manteuffel-Cymborowska (1999) Acta Biochim. Pol. 46:77-89; McKenna et al. (1999) J. Steroid Biochem. Mol. Biol. 69:3-12; Malik et al. (2000) Trends Biochem. Sci. 25:277-283; and Lemon et al. (1999) Curr. Opin. Genet. Dev. 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) Gene 245:21-29; Okanami et al. (1996) Genes Cells 1:87-99; Goff et al. (1991) Genes Dev. 5:298-309; Cho et al. (1999) Plant Mol. Biol. 40:419-429; Ulmason et al. (1999) Proc. Natl. Acad. Sci. USA 96:5844-5849; Sprenger-Haussels et al. (2000) Plant J. 22:1-8; Gong et al. (1999) Plant Mol. Biol. 41:33-44; and Hobo et al. (1999) Proc. Natl. Acad. Sci. USA 96:15,348-15,353.

Additional functional domains are disclosed, for example, in co-owned WO 00/41566. Further, insulator domains, chromatin remodeling proteins such as ISWI-containing domains and/or methyl binding domain proteins suitable for use in fusion molecules are described, for example, in co-owned International Publications WO 01/83793 and PCT/US01/42377.

In additional embodiments, targeted remodeling of chromatin, as disclosed, for example, in co-owned International Publication WO 01/83793, can be used to generate one or more sites in plant cell chromatin that are accessible to the binding of a functional domain/modified plant ZFP fusion molecule.

Fusion molecules are constructed by methods of cloning and biochemical conjugation that are well known to those of skill in the art. Fusion molecules comprise a modified plant ZFP binding domain and, for example, a transcriptional activation domain, a transcriptional repression domain, a component of a chromatin remodeling complex, an insulator domain or a functional fragment of any of these domains. In certain embodiments, fusion molecules comprise a modified plant zinc finger protein and at least two functional domains (e.g., an insulator domain or a methyl binding protein domain and, additionally, a transcriptional activation or repression domain). Fusion molecules also optionally comprise a nuclear localization signal (such as, for example, that from the SV40 T-antigen or the maize Opaque-2 NLS) and an epitope tag (such as, for example, FLAG or hemagglutinin). Fusion proteins (and nucleic acids encoding them) are designed such that the translational reading frame is preserved among the components of the fusion.

The fusion molecules disclosed herein comprise a modified plant zinc finger binding protein that binds to a target site. In certain embodiments, the target site is present in an accessible region of cellular chromatin. Accessible regions can be determined as described in co-owned International Publications WO 01/83751 and WO 01/83732. If the target site is not present in an accessible region of cellular chromatin, one or more accessible regions can be generated as described in co-owned International Publication WO 01/83793. In additional embodiments, one or more modified plant zinc finger components of a fusion molecule are capable of binding to cellular chromatin regardless of whether its target site is in an accessible region or not. For example, a ZFP as disclosed herein can be capable of binding to linker DNA and/or to nucleosomal DNA. Examples of this type of "pioneer" DNA binding domain are found in certain steroid receptors and in hepatocyte nuclear factor 3 (HNF3). Cordingley et al. (1987) *Cell* 48:261-270; Pina et al. (1990) *Cell* 60:719-731; and Cirillo et al. (1998) *EMBO J.* 17:244-254.

Methods of gene regulation using a functional domain, targeted to a specific sequence by virtue of a fused DNA binding domain, can achieve modulation of gene expression. Genes so modulated can be endogenous genes or exogenous genes. Modulation of gene expression can be in the form of repression (e.g., repressing expression of exogenous genes, for example, when the target gene resides in a pathological infecting microorganism, or repression of an endogenous gene of the subject, such as an oncogene or a viral receptor, that contributes to a disease state). As described herein, repression of a specific target gene can be achieved by using a fusion molecule comprising a modified plant zinc finger protein and a functional domain.

Alternatively, modulation can be in the form of activation, if activation of a gene (e.g., a tumor suppressor gene or a transgene) can ameliorate a disease state. In this case, a cell is contacted with any of the fusion molecules described herein, wherein the modified zinc finger portion of the fusion molecule is specific for the target gene. The target gene can be an exogenous gene such as, for example, a transgene, or it can be an endogenous cellular gene residing in cellular chromatin. The functional domain (e.g., insulator domain, activation domain, etc.) enables increased and/or sustained expression of the target gene.

For any such applications, the fusion molecule(s) and/or nucleic acids encoding one or more fusion molecules can be formulated with an acceptable carrier, to facilitate introduction into and/or expression in plant cells, as is known to those of skill in the art.

Polynucleotide and Polypeptide Delivery

The compositions described herein can be provided to the target cell in vitro or in vivo. In addition, the compositions can be provided as polypeptides, polynucleotides or combination thereof.

A. Delivery of Polynucleotides

In certain embodiments, the compositions are provided as one or more polynucleotides. Further, as noted above, a modified plant zinc finger protein-containing composition can be designed as a fusion between a polypeptide zinc finger and a functional domain that is encoded by a fusion nucleic acid. In both fusion and non-fusion cases, the nucleic acid can be cloned into intermediate vectors for transformation into prokaryotic or eukaryotic (e.g., plant) cells for replication and/or expression. Intermediate vectors for storage or manipulation of the nucleic acid or production of protein can be prokaryotic vectors, (e.g., plasmids), shuttle vectors, insect vectors, or viral vectors for example. A nucleic acid encoding a modified plant zinc finger protein can also cloned into an expression vector, for administration to a bacterial cell, fungal cell, protozoal cell, plant cell, or animal cell, preferably a plant cell.

To obtain expression of a cloned nucleic acid, it is typically subcloned into an expression vector that contains a promoter to direct transcription. Suitable bacterial and eukaryotic promoters are well known in the art and described, e.g., in Sambrook et al., supra; Ausubel et al., supra; and Kriegler, *Gene Transfer and Expression: A Laboratory Manual* (1990). Bacterial expression systems are available in, e.g., *E. coli, Bacillus* sp., and *Salmonella*. Palva et al. (1983) *Gene* 22:229-235. Kits for such expression systems are commercially available. Eukaryotic expression systems for mammalian cells, yeast, and insect cells are well known in the art and are also commercially available, for example, from Invitrogen, Carlsbad, Calif. and Clontech, Palo Alto, Calif.

Plant expression vectors and reporter genes are also generally known in the art. (See, e.g., Gruber et al. (1993) in *Methods of Plant Molecular Biology and Biotechnology*, CRC Press.) Such systems include in vitro and in vivo recombinant DNA techniques, and any other synthetic or natural recombination. (See, e.g., *Transgenic Plants: A Production System for Industrial and Pharmaceutical Proteins*, Owen and Pen eds., John Wiliey & Sons, 1996; *Transgenic Plants*, Galun and Breiman eds, Imperial College Press, 1997; *Applied Plant Biotechnology*, Chopra, Malik, and Bhat eds., Science Publishers, Inc., 1999.)

The promoter used to direct expression of the nucleic acid of choice depends on the particular application. For example, a strong constitutive promoter is typically used for expression and purification. In contrast, when a protein is to be used in vivo, either a constitutive or an inducible promoter is used, depending on the particular use of the protein. In addition, a weak promoter can be used, when low but sustained levels of protein are required. The promoter typically can also include elements that are responsive to transactivation, e.g., hypoxia response elements and small molecule control systems such as tet-regulated systems and the RU-486 system. See, e.g., Gossen et al. (1992) *Proc. Natl. Acad. Sci USA* 89:5547-5551; Oligino et al. (1998) *Gene Ther.* 5:491-496; Wang et al. (1997) *Gene Ther.* 4:432-441; Neering et al. (1996) *Blood* 88:1147-1155; and Rendahl et al. (1998) *Nat. Biotechnol.* 16:757-761.

Promoters suitable for use in plant expression systems include, but are not limited to, viral promoters such as the 35S RNA and 19S RNA promoters of cauliflower mosaic virus (CaMV) (Brisson et al. (1984) *Nature* 310:511-514, Example 1); the coat protein promoter of TMV (Takamatsu et al. (1987) *EMBO J.* 6:307-311); plant promoters such as the small subunit of RUBISCO (Coruzzi et al. (1984) *EMBO J.* 3:1671-1680; Broglie et al. (1984) *Science* 224:838-843; plant heat shock promoters, e.g., soybean hsp17.5-E or hsp17.3-B (Gurley et al. (1986) *Cell. Biol.* 6:559-565) may be used. Other examples of promoters that may be used in expression vectors comprising nucleotides encoding modified plant ZFPs include the promoter for the small subunit of ribulose-1,5-bis-phosphate carboxylase; promoters from tumor-inducing plasmids of *Agrobacterium tumefaciens*, such as the RUBISCO nopaline synthase (NOS) and octopine synthase promoters; bacterial T-DNA promoters such as mas and ocs promoters; or the figwort mosaic virus 35S promoter.

In a preferred embodiment, the modified plant ZFP polynucleotide sequence is under the control of the cauliflower mosaic virus (CaMV) 35S promoter (Example 3). The caulimorvirus family has provided a number of exemplary promoters for transgene expression in plants, in particular, the (CaMV) 35S promoter. (See, e.g., Kay et al. (1987) *Science* 236:1299.) Additional promoters from this family such as the figwort mosaic virus promoter, the Commelina yellow mottle virus promoter, and the rice tungro bacilliform virus promoter have been described in the art, and may also be used in the methods and compositions disclosed herein. (See, e.g., Sanger et al. (1990) *Plant Mol. Biol.* 14:433-443; Medberry et al. (1992) *Plant Cell* 4:195-192; Yin and Beachy (1995) *Plant J.* 7:969-980.)

The promoters may be modified, if desired, to affect their control characteristics. For example, the CaMV 35S promoter may be ligated to the portion of the RUBISCO gene that represses the expression of RUBISCO in the absence of light, to create a promoter that is active in leaves, but not in roots. The resulting chimeric promoter may be used as described herein. Constitutive plant promoters such as actin and ubiquitin, having general expression properties known in the art may be used to express modified plant ZFPs. (See, e.g., McElroy et al. (1990) *Plant Cell* 2:163-171; Christensen et al. (1992) *Plant Mol. Biol.* 18:675-689.)

Additionally, depending on the desired tissue, expression may be targeted to the endosperm, aleurone layer, embryo (or its parts as scutellum and cotyledons), pericarp, stem, leaves tubers, roots, etc. Examples of known tissue-specific promoters include the tuber-directed class I patatin promoter, the promoters associated with potato tuber ADPGPP genes, the soybean promoter of β-conglycinin (7S protein) which drives seed-directed transcription, and seed-directed promoters from the zein genes of maize endosperm. (See, e.g., Bevan et al., 1986, *Nucleic Acids Res.* 14: 4625-38; Muller et al., 1990, *Mol. Gen. Genet.* 224: 136-46; Bray, 1987, *Planta* 172: 364-370; Pedersen et al., 1982, *Cell* 29: 1015-26.) Additional seed-specific promoters include the phaseolin and napin promoters.

In addition to a promoter, an expression vector typically contains a transcription unit or expression cassette that contains additional elements required for the expression of the nucleic acid in host cells, either prokaryotic or eukaryotic. A typical expression cassette thus contains a promoter operably linked, e.g., to the nucleic acid sequence, and signals required, e.g., for efficient polyadenylation of the transcript, transcriptional termination, ribosome binding, and/or translation termination. Additional elements of the cassette may include, e.g., enhancers, and heterologous spliced intronic signals.

The particular expression vector used to transport the genetic information into the cell is selected with regard to the intended use of the resulting ZFP polypeptide, e.g., expression in plants.

In addition, the recombinant constructs may include plant-expressible selectable or screenable marker genes for isolating, identifying or tracking of plant cells transformed by these constructs. Selectable markers include, but are not limited to, genes that confer antibiotic resistances (e.g., resistance to kanamycin or hygromycin) or herbicide resistance (e.g., resistance to sulfonylurea, phosphinothricin, or glyphosate). Screenable markers include, but are not limited to, the genes encoding beta-glucuronidase (Jefferson (1987) *Plant Molec Biol. Rep* 5:387-405), luciferase (Ow et al. (1986) *Science* 234:856-859), and the B and C1 gene products that regulate anthocyanin pigment production (Goff et al. (1990) *EMBO J.* 9:2517-2522).

Other elements that are optionally included in expression vectors also include a replicon that functions in *E. coli* (or in the prokaryotic host, if other than *E. coli*), a selective marker that functions in a prokaryotic host, e.g., a gene encoding antibiotic resistance, to permit selection of bacteria that harbor recombinant plasmids, and unique restriction sites in nonessential regions of the vector to allow insertion of recombinant sequences.

Standard transfection methods can be used to produce bacterial, mammalian, yeast, insect, other cell lines or, preferably, plants that express large quantities of modified plant zinc finger proteins, which can be purified, if desired, using standard techniques. See, e.g., Colley et al. (1989) *J. Biol. Chem.* 264:17619-17622; and *Guide to Protein Purification, in Methods in Enzymology*, vol. 182 (Deutscher, ed.) 1990. Transformation of non-plant eukaryotic cells and prokaryotic cells are performed according to standard techniques. See, e.g., Morrison (1977) *J. Bacteriol.* 132:349-351; Clark-Curtiss et al. (1983) in *Methods in Enzymology* 101:347-362 (Wu et al., eds).

Transformation systems for plants as also known. (See, e.g., Weissbach & Weissbach, *Methods for Plant Molecular Biology*, Academic Press, NY, Section VIII, pp. 421-463 (1988); Grierson & Corey, *Plant Molecular Biology*, 2d Ed., Blackie, London, Ch. 7-9 (1988).) For example, *Agrobacterium* is often successfully employed to introduce nucleic acids into plants. Such transformation preferably uses binary *Agrobacterium* T-DNA vectors which can be used to transform dicotyledonous plants, monocotyledonous plants and plant cells (Bevan (1984) *Nuc. Acid Res.* 12:8711-8721; Horsch et al. (1985) *Science* 227:1229-1231; Bevan et al. (1982) *Ann. Rev. Genet* 16:357-384; Rogers et al. (1986) *Methods Enzymol.* 118:627-641; Hernalsteen et al. (1984) *EMBO J.* 3:3039-3041). In embodiments that utilize the *Agrobacterium* system for transforming plants, the recombinant DNA constructs typically comprise at least the right T-DNA border sequence flanking the DNA sequences to be transformed into the plant cell. In preferred embodiments, the sequences to be transferred are flanked by the right and left T-DNA border sequences. The design and construction of such T-DNA based transformation vectors are well known to those skilled in the art.

Other gene transfer and transformation methods include, but are not limited to, protoplast transformation through calcium-, polyethylene glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276); electroporation of plant tissues (D'Halluin et al.

(1992) *Plant Cell* 4:1495-1505); microinjection, silicon carbide mediated DNA uptake (Kaeppler et al. (1990) *Plant Cell Reporter* 9:415-418), microprojectile bombardment (see Klein et al. (1983) *Proc. Nat. Acad. Sci. USA* 85:4305-4309; and Gordon-Kamm et al. (1990) *Plant Cell* 2:603-618); direct gene transfer, in vitro protoplast transformation, plant virus-mediated transformation, liposome-mediated transformation, and ballistic particle acceleration (See, e.g., Paszkowski et al. (1984) *EMBO J.* 3:2717-2722; U.S. Pat. Nos. 4,684,611; 4,407,956; 4,536,475; Crossway et al., (1986) *Biotechniques* 4:320-334; Riggs et al (1986) *Proc. Natl. Acad. Sci USA* 83:5602-5606; Hinchee et al. (1988) *Biotechnology* 6:915-921; U.S. Pat. No. 4,945,050.)

A wide variety of host cells, plants and plant cell systems can be used, including, but not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*).

Modified plant ZFPs and the resulting gene product the ZFP modulates can also be produced from seed by way of seed-based production techniques using, for example, canola, corn, soybeans, rice and barley seed, and the modified plant ZFP, and/or sequences encoding it, can be recovered during seed germination. See, e.g., PCT Publication Numbers WO 9940210; WO 9916890; WO 9907206; U.S. Pat. No. 5,866,121; and U.S. Pat. No. 5,792,933; and all references cited therein.

B. Delivery of Polypeptides

In additional embodiments, modified plant ZFPs or fusion proteins comprising modified plant ZFPs are administered directly to target plant cells. In certain in vitro situations, the target cells are cultured in a medium containing a fusion protein comprising one or more functional domains fused to one or more of the modified plant ZFPs described herein. An important factor in the administration of polypeptide compounds in plants is ensuring that the polypeptide has the ability to traverse a cell wall. However, proteins, viruses, toxins, ballistic methods and the like have the ability to translocate polypeptides across a plant cell wall.

For example, "plasmodesmata" is the term given to explain cell-to-cell transport of endogenous and viral proteins and ribonucleoprotein complexes (RNPCs) in plants. Examples of viruses which can be linked to a modified plant zinc finger polypeptide (or fusion containing the same) for facilitating its uptake into plant cells include, tobacco mosaic virus (Oparka et al. (1997) *Plant J.* 12:781-789; rice phloem thioredoxin (Ishiwatari et al. (1998) *Planta* 205:12-22); potato virus X (Cruz et al. (1998) *Plant Cell* 10:495-510) and the like. Other suitable chemical moieties that provide enhanced cellular uptake can also be linked, either covalently or non-covalently, to the ZFPs. Toxin molecules also have the ability to transport polypeptides across cell walls.

Particle-mediated delivery techniques (e.g., ballistic injection) as described above regarding nucleic acids can also be used to introduce polypeptides into a plant cell.

Applications

The modified plant zinc finger proteins and fusion molecules disclosed herein, and expression vectors encoding these polypeptides, can be used to modulate the expression of, or the action of, any plant endogenous or exogenous gene or gene product. In such applications, modified plant ZFP-containing compositions can be administered directly to a plant, e.g., to facilitate the modulation of gene expression. Preferably, the modulated gene is endogenous, for example a gene involved in growth, development, morphology, seed or fruit-bearing ability and the like. The gene product itself may be isolated and, accordingly, modulation of endogenous plant genes can be achieved using plant-derived sequences.

Accordingly, expression of any gene in any organism, for example plants or fungi, can be modulated using the methods and compositions disclosed herein, including therapeutically relevant genes, genes of infecting microorganisms, viral genes, and genes whose expression is modulated in the processes of drug discovery and/or target validation. Such genes include, but are not limited to, Wilms' third tumor gene (WT3), vascular endothelial growth factors (VEGFs), VEGF receptors (e.g., flt and flk) CCR-5, low density lipoprotein receptor (LDLR), estrogen receptor, HER-2/neu, BRCA-1, BRCA-2, phosphoenolpyruvate carboxykinase (PEPCK), CYP7, fibrinogen, apolipoprotein A (ApoA), apolipoprotein B (ApoB), renin, phosphoenolpyruvate carboxykinase (PEPCK), CYP7, fibrinogen, nuclear factor κB (NF-κB), inhibitor of NF-κB (I-κB), tumor necrosis factors (e.g., TNF-α, TNF-β), interleukin-1 (IL-1), FAS (CD95), FAS ligand (CD95L), atrial natriuretic factor, platelet-derived factor (PDF), amyloid precursor protein (APP), tyrosinase, tyrosine hydroxylase, β-aspartyl hydroxylase, alkaline phosphatase, calpains (e.g., CAPN10) neuronal pentraxin receptor, adriamycin response protein, apolipoprotein E (apoE), leptin, leptin receptor, UCP-1, IL-1, IL-1 receptor, IL-2, IL-3, IL-4, IL-5, IL-6, IL-12, IL-15, interleukin receptors, G-CSF, GM-CSF, colony stimulating factor, erythropoietin (EPO), platelet-derived growth factor (PDGF), PDGF receptor, fibroblast growth factor (FGF), FGF receptor, PAF, p16, p19, p53, Rb, p21, myc, myb, globin, dystrophin, eutrophin, cystic fibrosis transmembrane conductance regulator (CFTR), GNDF, nerve growth factor (NGF), NGF receptor, epidermal growth factor (EGF), EGF receptor, transforming growth factors (e.g., TGF-α, TGF-β), fibroblast growth factor (FGF), interferons (e.g., IFN-α, IFN-β, and IFN-γ), insulin-related growth factor-1 (IGF-1), angiostatin, ICAM-1, signal transducer and activator of transcription (STAT), androgen receptors, e-cadherin, cathepsins (e.g., cathepsin W), topoisomerase, telomerase, bcl, bcl-2, Bax, T Cell-specific tyrosine kinase (Lck), p38 mitogen-activated protein kinase, protein tyrosine phosphatase (hPTP), adenylate cyclase, guanylate cyclase, α7 neuronal nicotinic acetylcholine receptor, 5-hydroxytryptamine (serotonin)-2A receptor, transcription elongation factor-3 (TEF-3), phosphatidylcholine transferase, ftz, PTI-1, polygalacturonase, EPSP synthase, FAD2-1, Δ-9 desaturase, Δ-12 desaturase, Δ-15 desaturase, acetyl-Coenzyme A carboxylase, acyl-ACP thioesterase, ADP-glucose pyrophosphorylase, starch synthase, cellulose synthase, sucrose synthase, fatty acid hydroperoxide lyase, and peroxisome proliferator-activated receptors, such as PPAR-γ2.

Expression of human, mammalian, bacterial, fungal, protozoal, Archaeal, plant and viral genes can be modulated; viral genes include, but are not limited to, hepatitis virus genes such as, for example, HBV-C, HBV-S, HBV-X and HBV-P; and HIV genes such as, for example, tat and rev. Modulation of expression of genes encoding antigens of a pathogenic organism can be achieved using the disclosed methods and compositions.

In other embodiments, the modulated gene can be exogenous, for example, a transgene that has been inserted into the plant. Techniques for generating transgenic plants are known in the art (see, e.g., Swain W F (1991) *TIBTECH* 9: 107-109; Ma J K C et al. (1994) *Eur J Immunology* 24:131-138; Hiatt A et al. (1992) *FEBS Letters* 307:71-75; Hein M B et al. (1991) *Biotechnology Progress* 7: 455-461; Duering K (1990) *Plant Molecular Biology* 15: 281-294). As with endogenous genes, the modified plant ZFP (or fusion polypeptides comprising the modified plant ZFPs described herein) can then modulate expression of a transgene, for example to produce a protein product of interest, without the need for regulatory molecules derived primarily from non-plant (e.g., animal) sources.

Accordingly, the compositions and methods disclosed herein can be used to facilitate a number of processes involving transcriptional regulation in plants. These processes include, but are not limited to, transcription, replication, recombination, repair, integration, maintenance of telomeres, processes involved in chromosome stability and disjunction, and maintenance and propagation of chromatin structures. The methods and compositions disclosed herein can be used to affect any of these processes, as well as any other process that can be influenced by ZFPs or ZFP fusions.

Additional exemplary applications for modulation of gene expression in plant cells using modified plant ZFPs include, for example, the optimization of crop traits affecting nutritional value, yield, stress tolerance, pathogen resistance, and resistance to agrochemicals (e.g. insecticides and/or herbicides). In addition, targeted gene regulation can be used to study gene function in plants, and to adapt plants for use as biological factories for the production of pharmaceutical compounds or industrial chemicals.

In preferred embodiments, one or more of the molecules described herein are used to achieve targeted activation or repression of gene expression, e.g., based upon the target site specificity of the modified plant ZFP. In another embodiment, one or more of the molecules described herein are used to achieve reactivation of a gene, for example a developmentally silenced gene; or to achieve sustained activation of a transgene. A modified plant ZFP can be targeted to a region outside of the coding region of the gene of interest and, in certain embodiments, is targeted to a region outside of known regulatory region(s) of the gene. In these embodiments, additional molecules, exogenous and/or endogenous, can optionally be used to facilitate repression or activation of gene expression. The additional molecules can also be fusion molecules, for example, fusions between a ZFP and a functional domain such as an activation or repression domain. See, for example, co-owned WO 00/41566.

In other applications, modified plant ZFPs and other DNA- and/or RNA-binding proteins are used in diagnostic methods for sequence-specific detection of target nucleic acid in a sample. For example, modified plant ZFPs can be used to detect variant alleles associated with a phenotype in a plant. As an example, modified plant ZFPs can be used to detect the presence of particular mRNA species or cDNA in a complex mixtures of mRNAs or cDNAs. As a further example, modified plant ZFPs can be used to quantify the copy number of a gene in a sample. A suitable format for performing diagnostic assays employs modified plant ZFPs linked to a domain that allows immobilization of the ZFP on a solid support such as, for example, a microtiter plate or an ELISA plate. The immobilized ZFP is contacted with a sample suspected of containing a target nucleic acid under conditions in which binding between the modified ZFP and its target sequence can occur. Typically, nucleic acids in the sample are labeled (e.g., in the course of PCR amplification). Alternatively, unlabelled nucleic acids can be detected using a second labeled probe nucleic acid. After washing, bound, labeled nucleic acids are detected. Labeling can be direct (i.e., the probe binds directly to the target nucleic acid) or indirect (i.e., probe binds to one or more molecules which themselves bind to the target). Labels can be, for example, radioactive, fluorescent, chemiluminescent and/or enzymatic.

Modified plant ZFPs, as disclosed herein, can also be used in assays that link phenotype to the expression of particular genes. Current methodologies for determination of gene function rely primarily upon either over-expressing a gene of interest or removing a gene of interest from its natural biological setting, and observing the effects. The phenotypic effects resulting from over-expression or knockout are then interpreted as an indication of the role of the gene in the biological system. Up- or down-regulation of gene expression using one or more modified plant ZFPs obviates the necessity of generating transgenic plants for use in these types of assay.

All references cited herein are hereby incorporated by reference in their entirety for all purposes.

The following examples are presented as illustrative of, but not limiting, the claimed subject matter.

EXAMPLES

Example 1

Production of Modified Plant Zinc Finger Binding Proteins

This example describes a strategy to select amino acid sequences for plant zinc finger backbones from among existing plant zinc finger sequences, and subsequent conceptual modification of the selected plant zinc finger amino acid sequences to optimize their DNA binding ability. Oligonucleotides used in the preparation of polynucleotides encoding proteins containing these zinc fingers in tandem array are then described.

A. Selection of Plant Zinc Finger Backbones

A search was conducted for plant zinc fingers whose backbone sequences (i.e., the portion of the zinc finger outside of the −1 through +6 portion of the recognition helix) resembled that of the SP-1 consensus sequence described by Berg (1992) *Proc. Natl. Acad. Sci. USA* 89:11,109-11,110. The sequences selected included the two conserved cysteine residues, a conserved basic residue (lysine or arginine) located two residues to the C-terminal side of the second (i.e. C-terminal) cysteine, a conserved phenylalanine residue located two residues to the C-terminal side of the basic residue, the two conserved histidine residues, and a conserved arginine residue located two residues to the C-terminal side of the first (i.e., N-terminal) conserved histidine. The amino acid sequences of these selected plant zinc finger backbones (compared to the SP-1 consensus sequence) are shown below, with conserved residues shown in bold and X referring to residues located at positions −1 through +6 in the recognition helix (which will differ among different proteins depending upon the target sequence):

```
SP-1            YKCPECGKSFSXXXXXXXHQRTHTGEKP    (SEQ ID NO: 11)
consensus:

F1:             KKKSKGHECPICFRVFKXXXXXXXHKRSHTGEKP   (SEQ ID NO: 12)

F2              YKCTVCGKSFSXXXXXXXHKRLHTGEKP    (SEQ ID NO: 13)

F3              FSCNYCQRKFYXXXXXXXHVRIH         (SEQ ID NO: 14)
                    -5   -1    5
```

The first finger (F1) was chosen because it contained a basic sequence N-terminal to the finger that is also found adjacent to the first finger of SP-1. The finger denoted F1 is a *Petunia* sequence, the F2 and F3 fingers are *Arabidopsis* sequences.

B. Modification of Plant Zinc Finger Backbones

Two of the three plant zinc fingers (F1 and F3, above) were modified so that their amino acid sequences more closely resembled the sequence of SP-1, as follows. (Note that the sequence of SP-1 is different from the sequence denoted "SP-1 consensus.") In F3, the Y residue at position −2 was converted to a G, and the sequence QNKK (SEQ ID NO: 15) was added to the C-terminus of F3. The QNKK sequence is present C-terminal to the third finger of SP-1, and permits greater flexibility of that finger, compared to fingers 1 and 2, which are flanked by the helix-capping sequence T G E K/R K/P (SEQ ID NO: 16). Such flexibility can be beneficial when the third finger is modified to contain a non-$C_2H_2$ structure. ** Finally, several amino acids were removed from the N-terminus of F1. The resulting zinc finger backbones had the following sequences:

```
KSKGHECPICFRVFKXXXXXXXHKRSHTGEKP    (SEQ ID NO: 17)

YKCTVCGKSFSXXXXXXXHKRLHTGEKP    (SEQ ID NO: 18)

FSCNYCQRKFGXXXXXXXHVRIHQNKK     (SEQ ID NO: 19)
```

Amino acid residues denoted by X, present in the recognition portion of these zinc fingers, are designed or selected depending upon the desired target site, according to methods disclosed, for example, in co-owned WO 00/41566 and WO 00/42219, and/or references cited supra.

C. Nucleic Acid Sequences Encoding Backbones for Modified Plant ZFPs

The following polynucleotide sequences are used for design of a three-finger plant ZFP that contains the F1, F2 and F3 backbones described above. Polynucleotides encoding multi-finger ZFPs are designed according to an overlapping oligonucleotide method as described in, for example, co-owned WO 00/41566 and WO 00/42219. Oligonucleotides H1, H2 and H3 (below) comprise sequences corresponding to the reverse complement of the recognition helices of fingers 1-3 respectively; accordingly, nucleotides denoted by N will vary depending upon the desired amino acid sequences of the recognition helices, which, in turn, will depend upon the nucleotide sequence of the target site. Oligonucleotides PB1, PB2 and PB3 encode the beta-sheet portions of the zinc fingers, which are common to all constructs. Codons used frequently in *Arabidopsis* and *E. coli* were selected for use in these oligonucleotides.

H1:
(SEQ ID NO: 20)
5'-CTC ACC GGT GTG AGA ACG CTT GTG NNN NNN NNN NNN NNN NNN NNN CTT GAA AAC ACG GAA-3'

H2:
(SEQ ID NO: 21)
5'-TTC ACC AGT ATG AAG ACG CTT ATG NNN NNN NNN NNN NNN NNN NNN AGA AAA AGA CTT ACC-3'

H3:
(SEQ ID NO: 22)
5'-CTT CTT GTT CTG GTG GAT ACG CAC GTG NNN NNN NNN NNN NNN NNN NNN ACC GAA CTT ACG CTG-3'

PB1:
(SEQ ID NO: 23)
5'-AAGTCTAAGGGTCACGAGTGCCCAATCTGCTTCCGTGTTTTC AAG-3'

PB2:
(SEQ ID NO: 24)
5'-TCTCACACCGGTGAGAAGCCATACAAGTGCACTGTTTGTGGTAAGTC TTTTTCT-3'

PB3:
(SEQ ID NO: 25)
5'-CTTCATACTGGTGAAAAGCCATTCTCTTGCAACTACTGCCAGCGTAA GTTCGGT-3'

Briefly, these six oligonucleotides are annealed and amplified by polymerase chain reaction. The initial amplification product is reamplified using primers that are complementary to the initial amplification product and that also contain 5' extensions containing restriction enzyme recognition sites, to facilitate cloning. The second amplification product is inserted into a vector containing, for example, one or more functional domains, nuclear localization sequences, and/or epitope tags. See, for example, co-owned WO 00/41566 and WO 00/42219.

Example 2

Construction of a Polynucleotide Encoding a Modified Plant Zinc Finger Protein for Binding to a Predetermined Target Sequence A modified plant zinc finger protein was designed to recognize the target sequence 5'-GAGGGGGCG-3' (SEQ ID NO:26). Recognition helix sequences for F1, F2 and F3 were determined, as shown in Table 1, and oligonucleotides corresponding to H1, H2 and H3 above, also including sequences encoding these recognition helices, were used for PCR assembly as described above.

TABLE 1

| Finger | Target | Helix sequence | Nucleotide sequence for PCR assembly |
|---|---|---|---|
| F1 | GCG | RSDELTR SEQ ID NO: 27 | 5'CTCACCGGTGTGAGAACGCTTGTGACGGGTCAACT CGTCAGAACGCTTGAAAACACGGAA-3' (SEQ ID NO: 28) |
| F2 | GGG | RSDHLTR SEQ ID NO: 29 | 5'TTCACCAGTATGAAGACGCTTATGACGGGTCAAGT GGTCAGAACGAGAAAAAGACTTACC-3' (SEQ ID NO: 30) |
| F3 | GAG | RSDNLTR SEQ ID NO: 31 | 5'CTTCTTGTTCTGGTGGATACGCACGTGACGGGTCA AGTTGTCAGAACGACCGAACTTACGCTG-3' (SEQ ID NO: 32) |

Subsequent to the initial amplification, a secondary amplification was conducted, as described above, using the following primers:

```
                                           (SEQ ID NO: 33)
PZF: 5'-CGGGGTACCAGGTAAGTCTAAGGGTCAC (SEQ ID NO: 34)
PZR: 5'-GCGCGGATCCACCCTTCTTGTTCTGGTGGATACG.
```

PZF includes a KpnI site (underlined) and overlaps the PB1 sequence (overlap indicated in bold). PZR includes a BamHI (underlined) site and overlaps with H3 (indicated in bold).

The secondary amplification product is digested with Kpn I and Bam HI and inserted into an appropriate vector (e.g., YCF3, whose construction is described below) to construct an expression vector encoding a modified plant ZFP fused to a functional domain, for modulation of gene expression in plant cells.

Example 3

Construction of Vectors for Expression of Modified Plant ZFPs

Figure 1B:
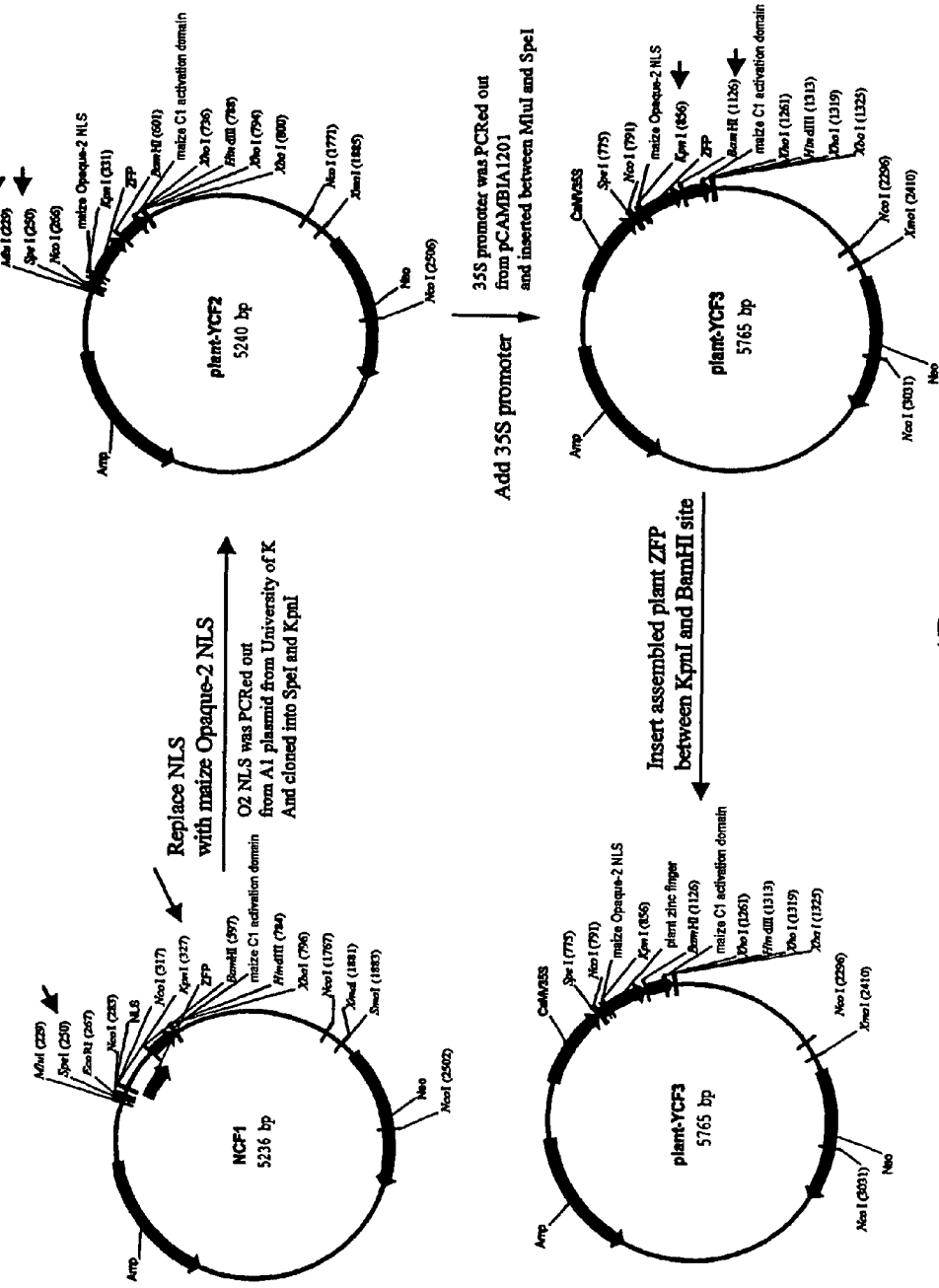

YCF3 was generated as shown schematically in FIG. 1. The starting construct was a plasmid containing a CMV promoter, a SV40 nuclear localization sequence (NLS), a ZFP DNA binding domain, a Herpesvirus VP16 transcriptional activation domain and a FLAG epitope tag (pSB5186-NVF). This construct was digested with SpeI to remove the CMV promoter. The larger fragment was gel-purified and self-ligated to make a plasmid termed GF1. GF1 was then digested with KpnI and HindIII, releasing sequences encoding the ZFP domain, the VP 16 activation domain, and the FLAG epitope tag, then the larger fragment was ligated to a KpnI/HindIII fragment containing sequences encoding a ZFP binding domain and a VP16 activation domain, named GF2. This resulted in deletion of sequences encoding the FLAG tag from the construct.

GF2 was digested with BamHI and HindIII, releasing a small fragment encoding the VP16 activation domain, and the larger fragment was purified and ligated to a BamHI/HindIII digested PCR fragment containing the maize C1 activation domain (Goff et al. (1990) *EMBO J.* 9:2517-2522) (KpnI and HindIII sites were introduced into the PCR fragment through KpnI and HindIII site-containing primers) to generate NCF1. A PCR fragment containing a Maize Opaque-2 NLS was digested with SpeI/KpnI and ligated to the larger fragment from KpnI/SpeI digested NCF1 to produce YCF2. YCF2 was then digested with MluI and SpeI and the larger fragment was ligated to an MluI and SpeI digested PCR fragment containing the plant-derived CaMV 35S promoter (MluI and SpeI sites were introduced into the PCR fragment through MluI or SpeI site containing primers) to generate the YCF3 vector.

Sequences encoding modified plant ZFP binding domains can be inserted, as KpnI/BamHI fragments, into KpnI/BamHI-digested YCF3 to generate constructs encoding ZFP-functional domain fusion proteins for modulation of gene expression in plant cells. For example, a series of modified plant ZFP domains, described in Example 4 infra, were inserted into KpnI/BamHI-digested YCF3 to generate expression vectors encoding modified plant ZFP-activation domain fusion polypeptides that enhance expression of the *Arabidopsis thaliana* GMT gene.

Example 4

Modified Plant ZFP Designs for Regulation of an *Arabidopsis thaliana* gamma tocopherol methyltransferase (GMT) Gene Modified plant zinc finger proteins were designed to recognize various target sequences in the *Arabidopsis* GMT gene (GenBank Accession Number AAD38271. Table 2 shows the nucleotide sequences of the various GMT target sites, and the amino acid sequences of zinc fingers that recognize the target sites. Sequences encoding these binding domains were prepared as described in Example 1 and inserted into YCF3 as described in Example 3.

TABLE 2

| ZFP # | Target | F1 | F2 | F3 |
|---|---|---|---|---|
| 1 | GTGGACGAGT (SEQ ID NO: 35) | RSDNLAR (SEQ ID NO: 36) | DRSNLTR (SEQ ID NO: 37) | RSDALTR (SEQ ID NO: 38) |
| 2 | CGGGATGGGT (SEQ ID NO: 39) | RSDHLAR (SEQ ID NO: 40) | TSGNLVR (SEQ ID NO: 41) | RSDHLRE (SEQ ID NO: 42) |
| 3 | TGGTGGGTGT (SEQ ID NO: 43) | RSDALTR (SEQ ID NO: 44) | RSDHLTT (SEQ ID NO: 45) | RSDHLTT (SEQ ID NO: 46) |

TABLE 2-continued

| ZFP # | Target | F1 | F2 | F3 |
|---|---|---|---|---|
| 4 | GAAGAGGATT (SEQ ID NO: 47) | QSSNLAR (SEQ ID NO: 48) | RSDNLAR (SEQ ID NO: 49) | QSGNLTR (SEQ ID NO: 50) |
| 5 | GAGGAAGGGG (SEQ ID NO: 51) | RSDHLAR (SEQ ID NO: 52) | QSGNLAR (SEQ ID NO: 53) | RSDNLTR (SEQ ID NO: 54) |
| 6 | TGGGTAGTC (SEQ ID NO: 55) | ERGTLAR (SEQ ID NO: 56) | QSGSLTR (SEQ ID NO: 57) | RSDHLTT (SEQ ID NO: 58) |
| 7 | GGGGAAAGGG (SEQ ID NO: 59) | RSDHLTQ (SEQ ID NO: 60) | QSGNLAR (SEQ ID NO: 61) | RSDHLSR (SEQ ID NO: 62) |
| 8 | GAAGAGGGTG (SEQ ID NO: 63) | QSSHLAR (SEQ ID NO: 64) | RSDNLAR (SEQ ID NO: 65) | QSGNLAR (SEQ ID NO: 66) |
| 9 | GACGAGGATG (SEQ ID NO: 67) | QSSNLQR (SEQ ID NO: 68) | RSDNALR (SEQ ID NO: 69) | RSDNLQR (SEQ ID NO: 70) |
| 10 | GAGGAGGAGG (SEQ ID NO: 71) | RSDNALR (SEQ ID NO: 72) | RSDNLAR (SEQ ID NO: 73) | RSDNLTR (SEQ ID NO: 74) |
| 11 | GTGGCGGCTG (SEQ ID NO: 75) | QSSDLRR (SEQ ID NO: 76) | RSDELQR (SEQ ID NO: 77) | RSDALTR (SEQ ID NO: 78) |
| 12 | TGGGGAGAT (SEQ ID NO: 79) | QSSNLAR (SEQ ID NO: 80) | QSGHLQR (SEQ ID NO: 81) | RSDHLTT (SEQ ID NO: 82) |
| 13 | GAGGAAGCT (SEQ ID NO: 83) | QSSDLRR (SEQ ID NO: 84) | QSGNLAR (SEQ ID NO: 85) | RSDNLTR (SEQ ID NO: 86) |
| 14 | GCTTGTGGCT (SEQ ID NO: 87) | DRSHLTR (SEQ ID NO: 88) | TSGHLTT (SEQ ID NO: 89) | QSSDLTR (SEQ ID NO: 90) |
| 15 | GTAGTGGATG (SEQ ID NO: 91) | QSSNLAR (SEQ ID NO: 92) | RSDALSR (SEQ ID NO: 93) | QSGSLTR (SEQ ID NO: 94) |
| 16 | GTGTGGGATT (SEQ ID NO: 95) | QSSNLAR (SEQ ID NO: 96) | RSDHLTT (SEQ ID NO: 97) | RSDALTR (SEQ ID NO: 98) |

Example 5

Modulation of Expression of an *Arabidopsis thaliana* Gamma Tocopherol Methyltransferase (GMT) Gene

*Arabidopsis thaliana* protoplasts were prepared and transfected with plasmids encoding modified ZFP-activation domain fusion polypeptides. Preparation of protoplasts and polyethylene glycol-mediated transfection were performed as described. Abel et al. (1994) *Plant Journal* 5:421-427. The different plasmids contained the modified plant ZFP binding domains described in Table 2, inserted as KpnI/BamHI fragments into YCF3.

Figure 2:
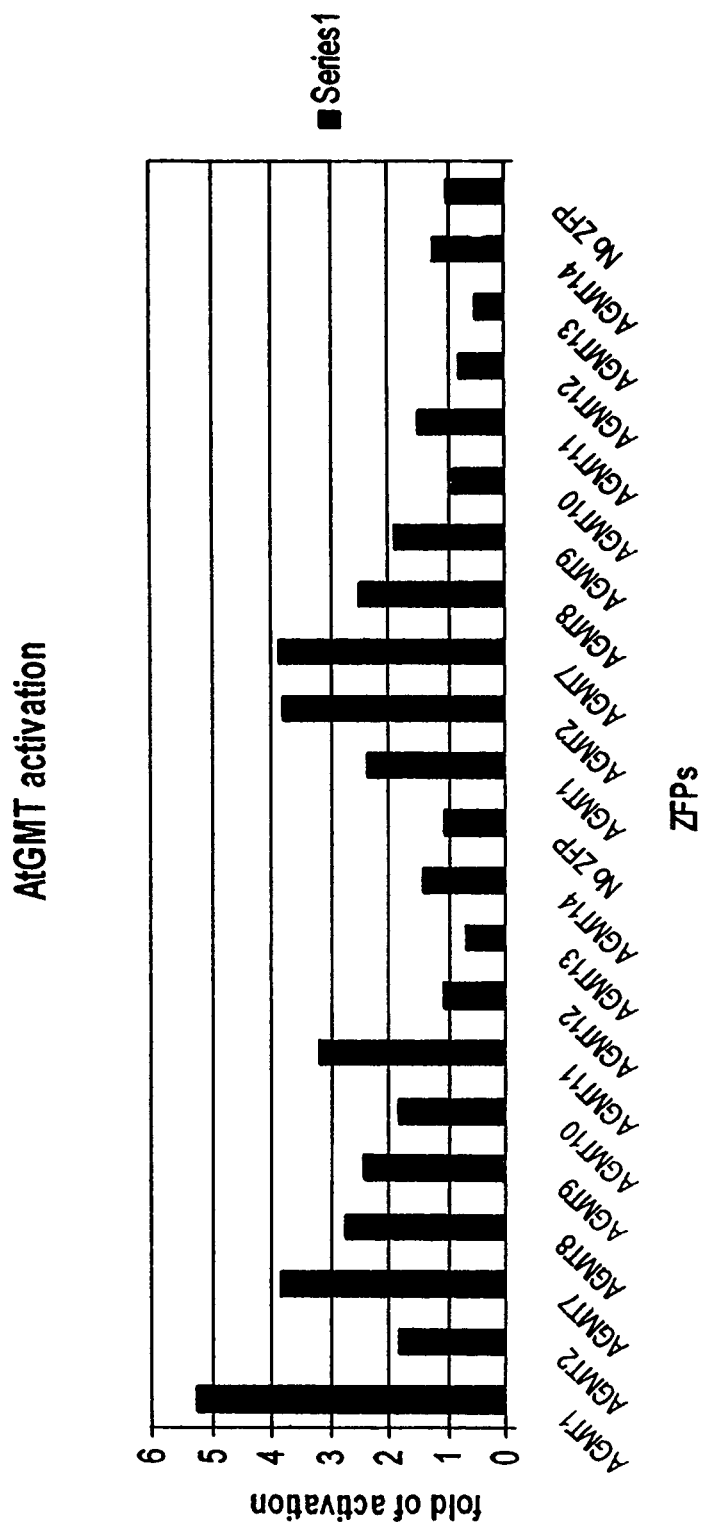
FIG. 2 shows the results of analysis of GMT mRNA in RNA isolated from *Arabidopsis thaliana* protoplasts that had been transfected with constructs encoding fusion of a transcriptional activation domain with various modified plant ZFPs. Results are expressed as GMT mRNA normalized to 18S rRNA. AGMT numbers on the abscissa refer to the modified plant ZFP binding domains shown in Table 2. Duplicate TaqMan® analyses are shown for each RNA sample.

At 18 hours after transfection, RNA was isolated from transfected protoplasts, using an RNA extraction kit from Qiagen (Valencia, Calif.) according to the manufacturer's instructions. The RNA was then treated with DNase (RNase-free), and analyzed for GMT mRNA content by real-time PCR (TaqMan®). Table 3 shows the sequences of the primers and probe used for TaqMan® analysis. Results for GMT mRNA levels were normalized to levels of 18S rRNA. These normalized results are shown in FIG. 2 as fold-activation of GMT mRNA levels, compared to protoplasts transfected with carrier DNA (denoted "No ZFP" in FIG. 2). The results indicate that expression of the GMT gene was enhanced in protoplasts that were transfected with plasmids encoding fusions between a transcriptional activation domain and a modified plant ZFP binding domain targeted to the GMT gene.

TABLE 3

| | SEQUENCE |
|---|---|
| GMT forward primer | 5'-AATGATCTCGCGGCTGCT-3' (SEQ ID NO: 99) |
| GMT reverse primer | 5'-GAATGGCTGATCCAACGCAT-3' (SEQ ID NO: 100) |
| GMT probe | 5'-TCACTCGCTCATAAGGCTTCCTTCCAAGT-3' (SEQ ID NO: 101) |
| 18S forward primer | 5'-TGCAACAAACCCCGACTTATG-3' (SEQ ID NO: 102) |
| 18S reverse primer | 5'-CCCGCGTCGACCTTTTATC-3' (SEQ ID NO: 103) |
| 18S probe | 5'-AATAAATGCGTCCCTT-3' (SEQ ID NO: 104) |

Although the foregoing methods and compositions have been described in detail for purposes of clarity of understanding, certain modifications, as known to those of skill in the art, can be practiced within the scope of the appended claims. All publications and patent documents cited herein are hereby incorporated by reference in their entirety for all purposes to the same extent as if each were so individually denoted.

What is claimed is:

1. A method of making a modified plant zinc finger protein comprising two or more zinc fingers, the method comprising the steps of:
    (a) providing a non-canonical plant zinc finger sequence comprising the sequence Cys-$(X)_{2-4}$-Cys-$(X)_{12}$-His-$(X)_{3-5}$-His (SEQ ID NO: 1), where X is any amino acid, wherein the C-terminal His residue is replaced with a Cys residue and all of the Cys and His residues are zinc coordinating residues and further wherein the 7 amino C-terminal residues of $(X)_{12}$ are the recognition helix region of the zinc finger and bind to target DNA;
    (b) modifying the non-canonical plant zinc finger sequence, wherein the modifying comprises making at least one substitution of at least one of the amino acid residues outside the recognition helix region and engineering the recognition helix region
    (c) combining the non-canonical plant zinc finger sequence with one or more additional plant canonical C2H2 zinc finger sequences into a zinc finger protein comprising two or more zinc fingers such that there are between 5 and 50 amino acids between adjacent zinc finger sequences, wherein the C-terminal zinc finger is the non-canonical plant zinc finger sequence thereby making a modified plant zinc finger protein.

2. The method of claim 1, wherein the recognition region is engineered to bind to the target sequence by rational design.

3. The method of claim 1, wherein the recognition region is engineered to bind to the target sequence by selection.

4. The method of claim 3, wherein selection is accomplished through the use of a method selected from the group consisting of phage display, interaction trap, ribosome display and RNA-peptide fusion.

5. The method of claim 1, wherein the target DNA has a sequence that is 3 or more contiguous nucleotides.

6. The method of claim 1, wherein the two or more zinc fingers are derived from two or more plant species.

7. The method of claim 1, wherein a polynucleotide encoding the modified plant zinc finger protein is synthesized.

* * * * *

SEQUENCE LISTING

<160> NUMBER OF SEQ ID NOS: 105

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: C2H2 zinc
      finger domain
<220> FEATURE:
<221> NAME/KEY: SITE
<222> LOCATION: (2)..(5)
<223> OTHER INFORMATION: Xaa = any amino acid
<220> FEATURE:
<221> NAME/KEY: SITE
<222> LOCATION: (4)..(5)
<223> OTHER INFORMATION: where Xaa may be present or absent
<220> FEATURE:
<221> NAME/KEY: SITE
<222> LOCATION: (7)..(18)
<223> OTHER INFORMATION: Xaa = any amino acid
<220> FEATURE:
<221> NAME/KEY: SITE
<222> LOCATION: (20)..(24)
<223> OTHER INFORMATION: Xaa = any amino acid
<220> FEATURE:
<221> NAME/KEY: SITE
<222> LOCATION: (23)..(24)
<223> OTHER INFORMATION: where Xaa may be present or absent

<400> SEQUENCE: 1

Cys Xaa Xaa Xaa Xaa Cys Xaa Xaa Xaa Xaa Xaa Xaa Xaa Xaa Xaa Xaa
 1               5                  10                  15

Xaa Xaa His Xaa Xaa Xaa Xaa Xaa His
            20                  25

<210> SEQ ID NO 2
<211> LENGTH: 9
<212> TYPE: DNA
<213> ORGANISM: Artificial Sequence
<220> FEATURE:
<223> OTHER INFORMATION: Description of Artificial Sequence: target
      sequence

<400> SEQUENCE: 2 ggcgtagac                                                                9

<210> SEQ ID NO 3
<211> LENGTH: 9
<212> TYPE: DNA
<213> ORGANISM: Artificial Sequence
<220> FEATURE:
<223> OTHER INFORMATION: Description of Artificial Sequence: target
      segment
<400> SEQUENCE: 3 ggcgacgta                                                                9

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: target
      sequence for 2 linked ZFPs
<220> FEATURE:
<221> NAME/KEY: misc_feature
<222> LOCATION: (1)..(23)
<223> OTHER INFORMATION: n = a, c, g or t
<220> FEATURE:
<221> NAME/KEY: misc_feature

```
<222> LOCATION: (1)..(3)
<223> OTHER INFORMATION: 3rd finger of a 2nd ZFP
<220> FEATURE:
<221> NAME/KEY: misc_feature
<222> LOCATION: (4)..(6)
<223> OTHER INFORMATION: 2nd finger of a 2nd ZFP
<220> FEATURE:
<221> NAME/KEY: misc_feature
<222> LOCATION: (7)..(9)
<223> OTHER INFORMATION: 1st finger of a 2nd ZFP
<220> FEATURE:
<221> NAME/KEY: misc_feature
<222> LOCATION: (10)..(14)
<223> OTHER INFORMATION: n may be present or absent
<220> FEATURE:
<221> NAME/KEY: misc_feature
<222> LOCATION: (15)..(17)
<223> OTHER INFORMATION: 3rd finger of a 1st ZFP
<220> FEATURE:
<221> NAME/KEY: misc_feature
<222> LOCATION: (18)..(20)
<223> OTHER INFORMATION: 2nd finger of a 1st ZFP
<220> FEATURE:
<221> NAME/KEY: misc_feature
<222> LOCATION: (21)..(23)
<223> OTHER INFORMATION: 1st finger of a 1st ZFP

<400> SEQUENCE: 4 nnnnnnnnn nnnnnnnnn nnn                                              23

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: peptide ZFP
      linker

<400> SEQUENCE: 5

Thr Gly Glu Lys Pro
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: peptide ZFP
      linker

<400> SEQUENCE: 6

Gly Gly Gly Gly Ser
 1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: peptide ZFP
      linker

<400> SEQUENCE: 7

Gly Gly Arg Arg Gly Gly Gly Ser
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: peptide ZFP
```

-continued

```
          linker

<400> SEQUENCE: 8

Leu Arg Gln Arg Asp Gly Glu Arg Pro
 1               5

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: peptide ZFP
      linker

<400> SEQUENCE: 9

Leu Arg Gln Lys Asp Gly Gly Gly Ser Glu Arg Pro
 1               5                  10

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: peptide ZFP
      linker

<400> SEQUENCE: 10

Leu Arg Gln Lys Asp Gly Gly Gly Ser Gly Gly Gly Ser Glu Arg Pro
 1               5                  10                  15

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: SP-1
      consensus ZFP recognition helix
<220> FEATURE:
<221> NAME/KEY: SITE
<222> LOCATION: (12)..(18)
<223> OTHER INFORMATION: Xaa = any amino acid

<400> SEQUENCE: 11

Tyr Lys Cys Pro Glu Cys Gly Lys Ser Phe Ser Xaa Xaa Xaa Xaa Xaa
 1               5                  10                  15

Xaa Xaa His Gln Arg Thr His Thr Gly Glu Lys Pro
            20                  25

<210> SEQ ID NO 12
<211> LENGTH: 34
<212> TYPE: PRT
<213> ORGANISM: Artificial Sequence
<220> FEATURE:
<223> OTHER INFORMATION: Description of Artificial Sequence: backbone F1
<220> FEATURE:
<221> NAME/KEY: SITE
<222> LOCATION: (18)..(24)
<223> OTHER INFORMATION: Xaa = any amino acid

<400> SEQUENCE: 12

Lys Lys Lys Ser Lys Gly His Glu Cys Pro Ile Cys Phe Arg Val Phe
 1               5                  10                  15

Lys Xaa Xaa Xaa Xaa Xaa Xaa Xaa His Lys Arg Ser His Thr Gly Glu
            20                  25                  30

Lys Pro

<210> SEQ ID NO 13
```

```
<211> LENGTH: 28
<212> TYPE: PRT
<213> ORGANISM: Artificial Sequence
<220> FEATURE:
<223> OTHER INFORMATION: Description of Artificial Sequence: backbone F2
<220> FEATURE:
<221> NAME/KEY: SITE
<222> LOCATION: (12)..(18)
<223> OTHER INFORMATION: Xaa = any amino acid

<400> SEQUENCE: 13

Tyr Lys Cys Thr Val Cys Gly Lys Ser Phe Ser Xaa Xaa Xaa Xaa Xaa
 1               5                  10                  15

Xaa Xaa His Lys Arg Leu His Thr Gly Glu Lys Pro
            20                  25

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: backbone F3
<220> FEATURE:
<221> NAME/KEY: SITE
<222> LOCATION: (12)..(18)
<223> OTHER INFORMATION: Xaa = any amino acid

<400> SEQUENCE: 14

Phe Ser Cys Asn Tyr Cys Gln Arg Lys Phe Tyr Xaa Xaa Xaa Xaa Xaa
 1               5                  10                  15

Xaa Xaa His Val Arg Ile His
            20

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: modified F1

<400> SEQUENCE: 15

Gln Asn Lys Lys
 1

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: helix-
      capping sequence
<220> FEATURE:
<221> NAME/KEY: SITE
<222> LOCATION: (4)
<223> OTHER INFORMATION: Xaa = either Lys or Arg
<220> FEATURE:
<221> NAME/KEY: SITE
<222> LOCATION: (5)
<223> OTHER INFORMATION: Xaa = either Lys or Pro

<400> SEQUENCE: 16

Thr Gly Glu Xaa Xaa
 1               5

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: modified
```

```
        backbone A
<220> FEATURE:
<221> NAME/KEY: SITE
<222> LOCATION: (16)..(22)
<223> OTHER INFORMATION: Xaa = any amino acid

<400> SEQUENCE: 17

Lys Ser Lys Gly His Glu Cys Pro Ile Cys Phe Arg Val Phe Lys Xaa
 1               5                  10                  15

Xaa Xaa Xaa Xaa Xaa Xaa His Lys Arg Ser His Thr Gly Glu Lys Pro
            20                  25                  30

<210> SEQ ID NO 18
<211> LENGTH: 28
<212> TYPE: PRT
<213> ORGANISM: Artificial Sequence
<220> FEATURE:
<223> OTHER INFORMATION: Description of Artificial Sequence: modified
      backbone B
<220> FEATURE:
<221> NAME/KEY: SITE
<222> LOCATION: (12)..(18)
<223> OTHER INFORMATION: Xaa = any amino acid

<400> SEQUENCE: 18

Tyr Lys Cys Thr Val Cys Gly Lys Ser Phe Ser Xaa Xaa Xaa Xaa Xaa
 1               5                  10                  15

Xaa Xaa His Lys Arg Leu His Thr Gly Glu Lys Pro
            20                  25

<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: modified
      backbone C
<220> FEATURE:
<221> NAME/KEY: SITE
<222> LOCATION: (12)..(18)
<223> OTHER INFORMATION: Xaa = any amino acid

<400> SEQUENCE: 19

Phe Ser Cys Asn Tyr Cys Gln Arg Lys Phe Gly Xaa Xaa Xaa Xaa Xaa
 1               5                  10                  15

Xaa Xaa His Val Arg Ile His Gln Asn Lys Lys
            20                  25

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence:
      oligonucleotide H1
<220> FEATURE:
<221> NAME/KEY: misc_feature
<222> LOCATION: (25)..(45)
<223> OTHER INFORMATION: n = any nucleotide

<400> SEQUENCE: 20
ctcaccggtg tgagaacgct tgtgnnnnnn nnnnnnnnnn nnnnncttga aaacacggaa       60

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence:
```

-continued

```
      oligonucleotide H2
<220> FEATURE:
<221> NAME/KEY: misc_feature
<222> LOCATION: (25)..(45)
<223> OTHER INFORMATION: n = any nucleotide

<400> SEQUENCE: 21
ttcaccagta tgaagacgct tatgnnnnnn nnnnnnnnnn nnnnnagaaa aagacttacc    60

<210> SEQ ID NO 22
<211> LENGTH: 63
<212> TYPE: DNA
<213> ORGANISM: Artificial Sequence
<220> FEATURE:
<223> OTHER INFORMATION: Description of Artificial Sequence:
      oligonucleotide H3
<220> FEATURE:
<221> NAME/KEY: misc_feature
<222> LOCATION: (28)..(48)
<223> OTHER INFORMATION: n = any nucleotide

<400> SEQUENCE: 22
cttcttgttc tggtggatac gcacgtgnnn nnnnnnnnnn nnnnnnnnac cgaacttacg    60
ctg                                                                 63

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence:
      oligonucleotide PB1

<400> SEQUENCE: 23
aagtctaagg gtcacgagtg cccaatctgc ttccgtgttt tcaag                    45

<210> SEQ ID NO 24
<211> LENGTH: 54
<212> TYPE: DNA
<213> ORGANISM: Artificial Sequence
<220> FEATURE:
<223> OTHER INFORMATION: Description of Artificial Sequence:
      oligonucleotide PB2

<400> SEQUENCE: 24
tctcacaccg gtgagaagcc atacaagtgc actgtttgtg gtaagtcttt ttct          54

<210> SEQ ID NO 25
<211> LENGTH: 54
<212> TYPE: DNA
<213> ORGANISM: Artificial Sequence
<220> FEATURE:
<223> OTHER INFORMATION: Description of Artificial Sequence:
      oligonucleotide PB3

<400> SEQUENCE: 25
cttcatactg gtgaaaagcc attctcttgc aactactgcc agcgtaagtt cggt          54

<210> SEQ ID NO 26
<211> LENGTH: 9
<212> TYPE: DNA
<213> ORGANISM: Artificial Sequence
<220> FEATURE:
<223> OTHER INFORMATION: Description of Artificial Sequence: target
      sequence

<400> SEQUENCE: 26 gaggggcg                                                             9
```

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: F1
      recognition helix
      sequence

<400> SEQUENCE: 27

Arg Ser Asp Glu Leu Thr Arg
  1               5

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: F1 PCR
      assembly sequence

<400> SEQUENCE: 28
ctcaccggtg tgagaacgct tgtgacgggt caactcgtca gaacgcttga aaacacggaa      60

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: F2
      recognition helix sequence

<400> SEQUENCE: 29

Arg Ser Asp His Leu Thr Arg
  1               5

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence: F2 PCR
      assembly sequence

<400> SEQUENCE: 30
ttcaccagta tgaagacgct tatgacgggt caagtggtca gaacgagaaa aagacttacc      60

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: F3
      recognition helix sequence

<400> SEQUENCE: 31

Arg Ser Asp Asn Leu Thr Arg
  1               5

<210> SEQ ID NO 32
<211> LENGTH: 63
<212> TYPE: DNA
<213> ORGANISM: Artificial Sequence
<220> FEATURE:
<223> OTHER INFORMATION: Description of Artificial Sequence: F3 PCR
      assembly sequence

<400> SEQUENCE: 32

```
cttcttgttc tggtggatac gcacgtgacg ggtcaagttg tcagaacgac cgaacttacg    60
ctg                                                                  63

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: primer PZF

<400> SEQUENCE: 33
cggggtacca ggtaagtcta agggtcac                                       28

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: primer PZR

<400> SEQUENCE: 34
gcgcggatcc acccttcttg ttctggtgga tacg                                34

<210> SEQ ID NO 35
<211> LENGTH: 10
<212> TYPE: DNA
<213> ORGANISM: Artificial Sequence
<220> FEATURE:
<223> OTHER INFORMATION: Description of Artificial Sequence: ZFP 1
      target sequence

<400> SEQUENCE: 35
gtggacgagt                                                           10

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: ZFP 1 F1
      recognition helix

<400> SEQUENCE: 36

Arg Ser Asp Asn Leu Ala Arg
 1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: ZFP 1 F2
      recognition helix

<400> SEQUENCE: 37

Asp Arg Ser Asn Leu Thr Arg
 1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence:  ZFP 1 F3
      recognition helix

<400> SEQUENCE: 38
```

-continued

Arg Ser Asp Ala Leu Thr Arg
 1               5

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: ZFP 2
      target sequence

<400> SEQUENCE: 39
cgggatgggt                                                           10

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: ZFP 2 F1
      recognition helix

<400> SEQUENCE: 40

Arg Ser Asp His Leu Ala Arg
 1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: ZFP 2 F2
      recognition helix

<400> SEQUENCE: 41

Thr Ser Gly Asn Leu Val Arg
 1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: ZFP 2 F3
      recognition helix

<400> SEQUENCE: 42

Arg Ser Asp His Leu Arg Glu
 1               5

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence: ZFP 3
      target sequence

<400> SEQUENCE: 43
tggtgggtgt                                                           10

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: ZFP 3 F1
      recognition helix -continued

```
<400> SEQUENCE: 44

Arg Ser Asp Ala Leu Thr Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: ZFP 3 F2
      recognition helix

<400> SEQUENCE: 45

Arg Ser Asp His Leu Thr Thr
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: ZFP 3 F3
      recognition helix

<400> SEQUENCE: 46

Arg Ser Asp His Leu Thr Thr
1               5

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: ZFP 4
      target sequence

<400> SEQUENCE: 47
gaagaggatt                                                          10

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: ZFP 4 F1
      recognition helix

<400> SEQUENCE: 48

Gln Ser Ser Asn Leu Ala Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: ZFP 4 F2
      recognition helix

<400> SEQUENCE: 49

Arg Ser Asp Asn Leu Ala Arg
1               5

<210> SEQ ID NO 50
<211> LENGTH: 7
<212> TYPE: PRT
<213> ORGANISM: Artificial Sequence
```

```
<220> FEATURE:
<223> OTHER INFORMATION: Description of Artificial Sequence: ZFP 4 F3
      recognition helix

<400> SEQUENCE: 50

Gln Ser Gly Asn Leu Thr Arg
 1               5

<210> SEQ ID NO 51
<211> LENGTH: 10
<212> TYPE: DNA
<213> ORGANISM: Artificial Sequence
<220> FEATURE:
<223> OTHER INFORMATION: Description of Artificial Sequence: ZFP 5
      target sequence

<400> SEQUENCE: 51
gaggaagggg                                                          10

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: ZFP 5 F1
      recognition helix

<400> SEQUENCE: 52

Arg Ser Asp His Leu Ala Arg
 1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: ZFP 5 F2
      recognition helix

<400> SEQUENCE: 53

Gln Ser Gly Asn Leu Ala Arg
 1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: ZFP 5 F3
      recognition helix

<400> SEQUENCE: 54

Arg Ser Asp Asn Leu Thr Arg
 1               5

<210> SEQ ID NO 55
<211> LENGTH: 9
<212> TYPE: DNA
<213> ORGANISM: Artificial Sequence
<220> FEATURE:
<223> OTHER INFORMATION: Description of Artificial Sequence: ZFP 6
      target sequence

<400> SEQUENCE: 55 tgggtagtc                                                            9

<210> SEQ ID NO 56
<211> LENGTH: 7
```

```
<212> TYPE: PRT
<213> ORGANISM: Artificial Sequence
<220> FEATURE:
<223> OTHER INFORMATION: Description of Artificial Sequence:  ZFP 6 F1
      recognition helix

<400> SEQUENCE: 56

Glu Arg Gly Thr Leu Ala Arg
  1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence:  ZFP 6 F2
      recognition helix

<400> SEQUENCE: 57

Gln Ser Gly Ser Leu Thr Arg
  1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence:  ZFP 6 F3
      recognition helix

<400> SEQUENCE: 58

Arg Ser Asp His Leu Thr Thr
  1               5

<210> SEQ ID NO 59
<211> LENGTH: 10
<212> TYPE: DNA
<213> ORGANISM: Artificial Sequence
<220> FEATURE:
<223> OTHER INFORMATION: Description of Artificial Sequence:  ZFP 7
      target sequence

<400> SEQUENCE: 59
ggggaaaggg                                                            10

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence:  ZFP 7 F1
      recognition helix

<400> SEQUENCE: 60

Arg Ser Asp His Leu Thr Gln
  1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence:  ZFP 7 F2
      recognition helix

<400> SEQUENCE: 61

Gln Ser Gly Asn Leu Ala Arg
  1               5
```

```
<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence:  ZFP 7 F3
      recognition helix

<400> SEQUENCE: 62

Arg Ser Asp His Leu Ser Arg
  1               5

<210> SEQ ID NO 63
<211> LENGTH: 10
<212> TYPE: DNA
<213> ORGANISM: Artificial Sequence
<220> FEATURE:
<223> OTHER INFORMATION: Description of Artificial Sequence:  ZFP 8
      target sequence

<400> SEQUENCE: 63
gaagagggtg                                                              10

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence:  ZFP 8 F1
      recognition helix

<400> SEQUENCE: 64

Gln Ser Ser His Leu Ala Arg
  1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence:  ZFP 8 F2
      recognition helix

<400> SEQUENCE: 65

Arg Ser Asp Asn Leu Ala Arg
  1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence:  ZFP 8 F3
      recognition helix

<400> SEQUENCE: 66

Gln Ser Gly Asn Leu Ala Arg
  1               5

<210> SEQ ID NO 67
<211> LENGTH: 10
<212> TYPE: DNA
<213> ORGANISM: Artificial Sequence
<220> FEATURE:
<223> OTHER INFORMATION: Description of Artificial Sequence:  ZFP 9
      target sequence

<400> SEQUENCE: 67
```

-continued gaggaggatg                                                            10

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: ZFP 9 F1
      recognition helix

<400> SEQUENCE: 68

Gln Ser Ser Asn Leu Gln Arg
  1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: ZFP 9 F2
      recognition helix

<400> SEQUENCE: 69

Arg Ser Asp Asn Ala Leu Arg
  1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: ZFP 9 F3
      recognition helix

<400> SEQUENCE: 70

Arg Ser Asp Asn Leu Gln Arg
  1               5

<210> SEQ ID NO 71
<211> LENGTH: 10
<212> TYPE: DNA
<213> ORGANISM: Artificial Sequence
<220> FEATURE:
<223> OTHER INFORMATION: Description of Artificial Sequence: ZFP 10
      target sequence

<400> SEQUENCE: 71
gaggaggagg                                                            10

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: ZFP 10 F1
      recognition helix

<400> SEQUENCE: 72

Arg Ser Asp Asn Ala Leu Arg
  1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: ZFP 10 F2
      recognition helix

```
<400> SEQUENCE: 73

Arg Ser Asp Asn Leu Ala Arg
  1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence:  ZFP 10 F3
      recognition helix

<400> SEQUENCE: 74

Arg Ser Asp Asn Leu Thr Arg
  1               5

<210> SEQ ID NO 75
<211> LENGTH: 10
<212> TYPE: DNA
<213> ORGANISM: Artificial Sequence
<220> FEATURE:
<223> OTHER INFORMATION: Description of Artificial Sequence:  ZFP 11
      target sequence

<400> SEQUENCE: 75
gtggcggctg                                                           10

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence:  ZFP 11 F1
      recognition helix

<400> SEQUENCE: 76

Gln Ser Ser Asp Leu Arg Arg
  1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence:  ZFP 11 F2
      recognition helix

<400> SEQUENCE: 77

Arg Ser Asp Glu Leu Gln Arg
  1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence:  ZFP 11 F3
      recognition helix

<400> SEQUENCE: 78

Arg Ser Asp Ala Leu Thr Arg
  1               5

<210> SEQ ID NO 79
<211> LENGTH: 9
<212> TYPE: DNA
<213> ORGANISM: Artificial Sequence
<220> FEATURE:
```

-continued

```
<223> OTHER INFORMATION: Description of Artificial Sequence: ZFP 12
      target sequence

<400> SEQUENCE: 79 tggggagat                                                              9

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: ZFP 12 F1
      recognition helix

<400> SEQUENCE: 80

Gln Ser Ser Asn Leu Ala Arg
 1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: ZFP 12 F2
      recognition helix

<400> SEQUENCE: 81

Gln Ser Gly His Leu Gln Arg
 1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: ZFP 12 F3
      recognition helix

<400> SEQUENCE: 82

Arg Ser Asp His Leu Thr Thr
 1               5

<210> SEQ ID NO 83
<211> LENGTH: 9
<212> TYPE: DNA
<213> ORGANISM: Artificial Sequence
<220> FEATURE:
<223> OTHER INFORMATION: Description of Artificial Sequence: ZFP 13
      target sequence

<400> SEQUENCE: 83 gaggaagct                                                              9

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: ZFP 13 F1
      recognition helix

<400> SEQUENCE: 84

Gln Ser Ser Asp Leu Arg Arg
 1               5

<210> SEQ ID NO 85
<211> LENGTH: 7
<212> TYPE: PRT
```

-continued

```
<213> ORGANISM: Artificial Sequence
<220> FEATURE:
<223> OTHER INFORMATION: Description of Artificial Sequence: ZFP 13 F2
      recognition helix

<400> SEQUENCE: 85

Gln Ser Gly Asn Leu Ala Arg
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: ZFP 13 F3
      recognition helix

<400> SEQUENCE: 86

Arg Ser Asp Asn Leu Thr Arg
1               5

<210> SEQ ID NO 87
<211> LENGTH: 10
<212> TYPE: DNA
<213> ORGANISM: Artificial Sequence
<220> FEATURE:
<223> OTHER INFORMATION: Description of Artificial Sequence: ZFP 14
      target sequence

<400> SEQUENCE: 87
gcttgtggct                                                        10

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: ZFP 14 F1
      recognition helix

<400> SEQUENCE: 88

Asp Arg Ser His Leu Thr Arg
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: ZFP 14 F2
      recognition helix

<400> SEQUENCE: 89

Thr Ser Gly His Leu Thr Thr
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: ZFP 14 F3
      recognition helix

<400> SEQUENCE: 90

Gln Ser Ser Asp Leu Thr Arg
1               5
```

```
<210> SEQ ID NO 91
<211> LENGTH: 10
<212> TYPE: DNA
<213> ORGANISM: Artificial Sequence
<220> FEATURE:
<223> OTHER INFORMATION: Description of Artificial Sequence:  ZFP 15
      target sequence

<400> SEQUENCE: 91
gtagtggatg                                                                 10

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence:  ZFP 15 F1
      recognition helix

<400> SEQUENCE: 92

Gln Ser Ser Asn Leu Ala Arg
 1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence:  ZFP 15 F2
      recognition helix

<400> SEQUENCE: 93

Arg Ser Asp Ala Leu Ser Arg
 1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence:  ZFP 15 F3
      recognition helix

<400> SEQUENCE: 94

Gln Ser Gly Ser Leu Thr Arg
 1               5

<210> SEQ ID NO 95
<211> LENGTH: 10
<212> TYPE: DNA
<213> ORGANISM: Artificial Sequence
<220> FEATURE:
<223> OTHER INFORMATION: Description of Artificial Sequence:  ZFP 16
      target sequence

<400> SEQUENCE: 95
gtgtgggatt                                                                 10

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence:  ZFP 16 F1
      recognition helix

<400> SEQUENCE: 96

Gln Ser Ser Asn Leu Ala Arg
 1               5
```

-continued

```
<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence:  ZFP 16 F2
      recognition helix

<400> SEQUENCE: 97

Arg Ser Asp His Leu Thr Thr
  1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence:  ZFP 16 F3
      recognition helix

<400> SEQUENCE: 98

Arg Ser Asp Ala Leu Thr Arg
  1               5

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence: GMT forward
      primer

<400> SEQUENCE: 99
aatgatctcg cggctgct                                                   18

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: GMT reverse
      primer

<400> SEQUENCE: 100
gaatggctga tccaacgcat                                                 20

<210> SEQ ID NO 101
<211> LENGTH: 29
<212> TYPE: DNA
<213> ORGANISM: Artificial Sequence
<220> FEATURE:
<223> OTHER INFORMATION: Description of Artificial Sequence: GMT probe

<400> SEQUENCE: 101
tcactcgctc ataaggcttc cttccaagt                                       29

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: 18S forward
      primer

<400> SEQUENCE: 102
tgcaacaaac cccgacttat g                                               21
```

```
<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: 18S reverse
      primer

<400> SEQUENCE: 103
cccgcgtcga ccttttatc                                                   19

<210> SEQ ID NO 104
<211> LENGTH: 16
<212> TYPE: DNA
<213> ORGANISM: Artificial Sequence
<220> FEATURE:
<223> OTHER INFORMATION: Description of Artificial Sequence: 18S probe

<400> SEQUENCE: 104
aataaatgcg tccctt                                                      16

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: recognition
      sequence

<400> SEQUENCE: 105

Gln Ala Leu Gly Gly His
 1               5
```